United States Patent
Belson et al.

(10) Patent No.: US 10,123,801 B2
(45) Date of Patent: Nov. 13, 2018

(54) MEANS TO PREVENT WOUND DRESSINGS FROM ADHERING TO CLOSURE DEVICE

(71) Applicant: ZIPLINE MEDICAL, INC., Campbell, CA (US)

(72) Inventors: Amir Belson, Los Altos, CA (US); Eric Storne, Menlo Park, CA (US); Jeremy Edinger, Campbell, CA (US); Zachary Kimura, Campbell, CA (US); Alan Schaer, San Jose, CA (US); Keiichiro Ichiryu, Campbell, CA (US)

(73) Assignee: ZipLine Medical, Inc., Campbell, CA (US)

( * ) Notice: Subject to any disclaimer, the term of this patent is extended or adjusted under 35 U.S.C. 154(b) by 0 days.

(21) Appl. No.: 15/130,764

(22) Filed: Apr. 15, 2016

(65) Prior Publication Data
US 2017/0035422 A1    Feb. 9, 2017

Related U.S. Application Data

(60) Provisional application No. 62/202,572, filed on Aug. 7, 2015.

(51) Int. Cl.
*A61B 17/08* (2006.01)
*A61B 17/00* (2006.01)
*A61F 13/00* (2006.01)

(52) U.S. Cl.
CPC .. *A61B 17/085* (2013.01); *A61B 2017/00849* (2013.01); *A61B 2017/00889* (2013.01);
(Continued)

(58) Field of Classification Search
CPC . A61B 17/08; A61B 17/085; A61B 2017/081; A61B 2017/086;
(Continued)

(56) References Cited

U.S. PATENT DOCUMENTS

| | | |
|---|---|---|
| 2,012,755 A | 8/1935 | Muth |
| 2,371,978 A | 3/1945 | Perham |

(Continued)

FOREIGN PATENT DOCUMENTS

| | | |
|---|---|---|
| CN | 1126430 A | 7/1996 |
| CN | 1442119 A | 9/2003 |

(Continued)

OTHER PUBLICATIONS

Co-pending U.S. Appl. No. 15/081,526, filed Mar. 25, 2016.
(Continued)

*Primary Examiner* — Ryan J Severson
*Assistant Examiner* — Christian Knauss
(74) *Attorney, Agent, or Firm* — Wilson Sonsini Goodrich and Rosati, P.C.

(57) ABSTRACT

A wound dressing for use with a closure device is disclosed. The first and second base panels of the closure device are positioned on opposite lateral sides of a wound or incision. The base panels are coupled together to maintain wound or incision closure. A release liner is removed from a bottom surface of the wound dressing. The wound dressing is positioned over the closure device and the wound or incision. Exudate is absorbed by an absorbent material of the wound dressing through a porous strip of the wound dressing. The wound dressing is slightly larger than the closure device so that its perimeter area is adhered to the skin area around the closure device. Alternatively or in combination, the wound dressing is lightly adhered to the closure device and wound or incision area so that it can be removed without harming the underlying device and tissues.

13 Claims, 20 Drawing Sheets

(52) U.S. Cl.
CPC ... *A61B 2017/081* (2013.01); *A61B 2017/086* (2013.01); *A61F 13/00051* (2013.01)

(58) Field of Classification Search
CPC .... A61B 2017/088; A61B 2017/00884; A61B 2017/00889; A61F 2013/00217
See application file for complete search history.

(56) References Cited

U.S. PATENT DOCUMENTS

| | | |
|---|---|---|
| 2,747,248 A | 5/1956 | Mercer |
| 3,118,201 A | 1/1964 | Beghetto, Jr. |
| 3,487,836 A | 1/1970 | Niebel et al. |
| 3,516,409 A | 6/1970 | Howell |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 4,038,989 A | 8/1977 | Romero-Sierra et al. |
| 4,114,624 A | 9/1978 | Haverstock |
| 4,210,148 A | 7/1980 | Stivala |
| 4,222,383 A | 9/1980 | Schossow |
| 4,224,945 A | 9/1980 | Cohen |
| 4,526,173 A | 7/1985 | Sheehan |
| 4,531,521 A | 7/1985 | Haverstock |
| 4,535,772 A | 8/1985 | Sheehan |
| 4,539,990 A | 9/1985 | Stivala |
| 4,576,163 A | 3/1986 | Bliss |
| 4,605,005 A | 8/1986 | Sheehan |
| 4,676,245 A | 6/1987 | Fukuda |
| 4,702,251 A | 10/1987 | Sheehan |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A * | 12/1990 | Haverstock ........... A61B 17/085 606/213 |
| 5,176,703 A | 1/1993 | Peterson |
| 5,190,032 A * | 3/1993 | Zacoi ................... A61F 7/02 607/104 |
| 5,259,835 A | 11/1993 | Clark et al. |
| 5,306,236 A | 4/1994 | Blumenfeld et al. |
| 5,336,219 A | 8/1994 | Krantz |
| 5,377,695 A | 1/1995 | An Haack |
| 5,514,155 A | 5/1996 | Daneshvar |
| 5,533,519 A | 7/1996 | Radke et al. |
| 5,562,705 A | 10/1996 | Whiteford |
| 5,665,108 A | 9/1997 | Galindo |
| 5,725,507 A | 3/1998 | Petrick |
| 5,788,660 A | 8/1998 | Resnik |
| 5,823,983 A | 10/1998 | Rosofsky et al. |
| 5,843,123 A * | 12/1998 | Brazeau ............... A61B 17/085 606/213 |
| 6,007,564 A | 12/1999 | Haverstock |
| 6,033,654 A | 3/2000 | Stedronsky et al. |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,629,949 B1 | 10/2003 | Douglas |
| 6,689,100 B2 | 2/2004 | Connelly et al. |
| 6,726,706 B2 | 4/2004 | Dominguez |
| 7,066,182 B1 | 6/2006 | Dunshee |
| 7,361,185 B2 | 4/2008 | O'Malley et al. |
| 7,455,681 B2 | 11/2008 | Wilke et al. |
| 7,511,185 B2 | 3/2009 | Lebner |
| 7,641,682 B2 | 1/2010 | Palmaz et al. |
| 7,645,285 B2 | 1/2010 | Cosgrove et al. |
| 7,799,042 B2 | 9/2010 | Williamson et al. |
| 8,246,590 B2 | 8/2012 | Hu et al. |
| 8,313,508 B2 | 11/2012 | Belson et al. |
| 8,323,313 B1 | 12/2012 | Belson et al. |
| 8,439,945 B2 | 5/2013 | Belson et al. |
| 8,592,640 B2 | 11/2013 | Zepeda et al. |
| 8,663,275 B2 | 3/2014 | O'Malley et al. |
| 9,008,784 B2 | 4/2015 | Chan et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,271,858 B2 | 3/2016 | Ben-Meir et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Belson et al. |
| 9,642,621 B2 | 5/2017 | Belson et al. |
| 9,642,622 B2 | 5/2017 | Belson et al. |
| 2002/0099315 A1 | 7/2002 | Lebner |
| 2003/0065294 A1 | 4/2003 | Pickup et al. |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 * | 4/2004 | Udding ................ C08G 18/68 525/453 |
| 2004/0106904 A1 | 6/2004 | Gonnelli et al. |
| 2004/0204740 A1 | 10/2004 | Weiser |
| 2004/0210176 A1 | 10/2004 | Diana |
| 2004/0260234 A1 | 12/2004 | Srinivasan et al. |
| 2005/0020956 A1 | 1/2005 | Lebner |
| 2005/0020957 A1 | 1/2005 | Lebner |
| 2005/0070956 A1 | 3/2005 | Rousseau |
| 2005/0080453 A1 | 4/2005 | Lebner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 * | 12/2005 | Tacklind ............. A61B 17/085 209/132 |
| 2006/0030886 A1 | 2/2006 | Clark |
| 2006/0122522 A1 | 6/2006 | Chavan et al. |
| 2006/0200198 A1 | 9/2006 | Riskin et al. |
| 2006/0259033 A1 * | 11/2006 | Nesbitt ............... A61B 18/1402 606/45 |
| 2007/0026078 A1 | 2/2007 | Almarsson et al. |
| 2007/0038247 A1 | 2/2007 | Lebner et al. |
| 2007/0078366 A1 | 4/2007 | Haggstrom et al. |
| 2007/0088339 A1 | 4/2007 | Luchetti et al. |
| 2007/0106277 A1 | 5/2007 | Hood et al. |
| 2007/0141130 A1 | 6/2007 | Villanueva et al. |
| 2007/0179419 A1 | 8/2007 | Simpson |
| 2007/0185432 A1 | 8/2007 | Etheredge, III |
| 2007/0260278 A1 | 11/2007 | Wheeler et al. |
| 2008/0033334 A1 | 2/2008 | Gurtner et al. |
| 2008/0069855 A1 | 3/2008 | Bonutti |
| 2008/0081951 A1 | 4/2008 | Frasier et al. |
| 2008/0103550 A1 | 5/2008 | Wenzel et al. |
| 2008/0114396 A1 | 5/2008 | Cory et al. |
| 2008/0147115 A1 | 6/2008 | O'Malley et al. |
| 2008/0161731 A1 | 7/2008 | Woods et al. |
| 2008/0228219 A1 * | 9/2008 | Weiser ............... A61B 17/085 606/215 |
| 2008/0287864 A1 | 11/2008 | Rosenberg |
| 2009/0036922 A1 | 2/2009 | Riskin et al. |
| 2009/0062531 A1 | 3/2009 | Kanda |
| 2009/0099496 A1 | 4/2009 | Heegaard et al. |
| 2009/0149869 A1 | 6/2009 | Lhun |
| 2009/0158131 A1 | 6/2009 | Choi et al. |
| 2009/0162531 A1 * | 6/2009 | Nesbitt ............... A61L 29/085 427/2.12 |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2010/0280545 A1 | 11/2010 | Fridman |
| 2011/0077667 A1 | 3/2011 | Singhatat et al. |

(56) References Cited

U.S. PATENT DOCUMENTS

| | | |
|---|---|---|
| 2011/0106026 A1 | 5/2011 | Wu et al. |
| 2011/0144470 A1 | 6/2011 | Mazar et al. |
| 2012/0016410 A1 | 1/2012 | Belson et al. |
| 2012/0029266 A1 | 2/2012 | Holmes et al. |
| 2012/0095502 A1 | 4/2012 | Bargon et al. |
| 2012/0116279 A1 | 5/2012 | Munro et al. |
| 2012/0116485 A1 | 5/2012 | Burgmann |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0267928 A1 | 10/2013 | Imran et al. |
| 2013/0281885 A1 | 10/2013 | Rowbottom et al. |
| 2013/0281981 A1 | 10/2013 | Shamir |
| 2013/0282049 A1 | 10/2013 | Peterson et al. |
| 2013/0296930 A1 | 11/2013 | Belson et al. |
| 2013/0331757 A1 | 12/2013 | Belson |
| 2014/0074156 A1 | 3/2014 | Belson et al. |
| 2014/0171849 A1 | 6/2014 | Fischell et al. |
| 2014/0222070 A1 | 8/2014 | Belson et al. |
| 2014/0228712 A1 | 8/2014 | Elliott et al. |
| 2014/0278229 A1 | 9/2014 | Hong et al. |
| 2014/0316323 A1 | 10/2014 | Kanevsky et al. |
| 2015/0045700 A1 | 2/2015 | Cavanagh et al. |
| 2015/0105423 A1 | 4/2015 | Haudenschild et al. |
| 2015/0148653 A1 | 5/2015 | Fleig et al. |
| 2015/0209563 A1 | 7/2015 | Amir |
| 2015/0216527 A1 | 8/2015 | Belson et al. |
| 2015/0309535 A1 | 10/2015 | Connor et al. |
| 2015/0313593 A1 | 11/2015 | Patenaude et al. |
| 2015/0351690 A1 | 12/2015 | Toth et al. |
| 2016/0007909 A1 | 1/2016 | Singh et al. |
| 2016/0095597 A1 | 4/2016 | Belson et al. |
| 2016/0106931 A1 | 4/2016 | Belson et al. |
| 2016/0114146 A1 | 4/2016 | Belson et al. |
| 2016/0202755 A1 | 7/2016 | Connor |
| 2016/0206311 A1 | 7/2016 | Belson et al. |
| 2016/0206312 A1 | 7/2016 | Belson et al. |
| 2016/0206313 A1 | 7/2016 | Belson et al. |
| 2016/0213924 A1 | 7/2016 | Coleman et al. |
| 2016/0220175 A1 | 8/2016 | Tam et al. |
| 2016/0220252 A1 | 8/2016 | Belson et al. |
| 2016/0242646 A1 | 8/2016 | Obma |
| 2016/0249924 A1 | 9/2016 | Belson et al. |
| 2016/0296149 A1 | 10/2016 | Polsky et al. |
| 2016/0302721 A1 | 10/2016 | Wiedenhoefer et al. |
| 2016/0310140 A1 | 10/2016 | Belson et al. |
| 2017/0042541 A1 | 2/2017 | Belson et al. |
| 2017/0143341 A1 | 5/2017 | Belson et al. |
| 2017/0156664 A1 | 6/2017 | Belson et al. |

FOREIGN PATENT DOCUMENTS

| | | |
|---|---|---|
| CN | 1524507 A | 9/2004 |
| CN | 1234327 C | 1/2006 |
| CN | 101938944 A | 1/2011 |
| CN | 202537562 U | 11/2012 |
| CN | 102946812 A | 2/2013 |
| CN | 104755033 A | 7/2015 |
| CN | 104825200 A | 8/2015 |
| EP | 1600108 A2 | 11/2005 |
| GB | 1401877 A | 8/1975 |
| JP | H07502913 A | 3/1995 |
| JP | 2001149485 A | 6/2001 |
| JP | 2005512678 A | 5/2005 |
| JP | 2005532134 A | 10/2005 |
| JP | 2010504835 A | 2/2010 |
| JP | 2013515417 A | 5/2013 |
| JP | 2013538603 A | 10/2013 |
| WO | WO-8401805 A1 | 5/1984 |
| WO | WO-9629013 A1 | 9/1996 |
| WO | WO-03053296 A1 | 7/2003 |
| WO | WO-2006124671 A2 | 11/2006 |
| WO | WO-2007004603 A1 | 1/2007 |
| WO | WO-2007044647 A2 | 4/2007 |
| WO | WO-2008019051 A2 | 2/2008 |
| WO | WO-2008060532 A2 | 5/2008 |
| WO | WO-2009066116 A1 | 5/2009 |
| WO | WO-2011019859 A2 | 2/2011 |
| WO | WO-2011019859 A3 | 4/2011 |
| WO | WO-2011043786 A1 | 4/2011 |
| WO | WO-2011139912 A1 | 11/2011 |
| WO | WO-2011159623 A1 | 12/2011 |
| WO | WO-2013067024 A1 | 5/2013 |
| WO | WO-2014066879 A2 | 5/2014 |
| WO | WO-2014070922 A1 | 5/2014 |
| WO | WO-2015012887 A1 | 1/2015 |
| WO | WO-2015103556 A1 | 7/2015 |
| WO | WO-2015168165 A1 | 11/2015 |
| WO | WO-2017027075 A1 | 2/2017 |
| WO | WO-2017044120 A1 | 3/2017 |
| WO | WO-2017181059 A1 | 10/2017 |
| WO | WO-2017184825 A1 | 10/2017 |

OTHER PUBLICATIONS

Co-pending U.S. Appl. No. 15/081,550, filed Mar. 25, 2016.
Co-pending U.S. Appl. No. 15/081,595, filed Mar. 25, 2016.
European search report and opinion dated Jan. 7, 2014 for EP Application No. 11778067.6.
European search report and opinion dated Jan. 7, 2014 for EP Application No. 11796253.0.
European search report and opinion dated Apr. 29, 2015 for EP Application No. 10822334.8.
European search report and written opinion dated Aug. 12, 2015 for EP Application No. 12844746.3.
Hasson, et al. A new sutureless technique for skin closure. Arch Surg. Jan. 1976;111(1):83-4.
International search report and written opinion dated Jan. 12, 2016 for PCT Application No. US2015/049671.
International search report and written opinion dated Feb. 6, 2014 for PCT/US2013/067563.
International search report and written opinion dated Mar. 19, 2013 for PCT/US2012/062820.
International search report and written opinion dated Apr. 29, 2015 for PCT/US2015/010188.
International search report and written opinion dated Jul. 29, 2011 for PCT/US2011/034649.
International search report and written opinion dated Jul. 30, 2010 for PCT/US2010/000430.
International search report and written opinion dated Sep. 10, 2014 for PCT/US2014/016587.
International search report and written opinion dated Sep. 30, 2015 for PCT Application No. US2015/28066.
International search report and written opinion dated Oct. 21, 2011 for PCT Application No. US11/40213.
K984204, 510(k) Premarket Notification Summary, Silverlon™ Direct Pressure Wound Closure Strip, May 19, 2007.
Merriam-Webster Dictionary. Definition of "lateral". Http://www.merriam-webster.com/dictionary/lateral. Accessed on May 5, 2016.
Notice of allowance dated Jan. 17, 2013 for U.S. Appl. No. 13/096,602.
Notice of allowance dated Feb. 10, 2015 for U.S. Appl. No. 14/180,524.
Notice of allowance dated Jun. 21, 2016 for U.S. Appl. No. 15/081,526.
Notice of allowance dated Sep. 17, 2012 for U.S. Appl. No. 13/286,378.
Notice of allowance dated Sep. 20, 2012 for U.S. Appl. No. 13/286,757.
Notice of allowance dated Sep. 22, 2015 for U.S. Appl. No. 13/414,176.
Notice of allowance dated Dec. 19, 2014 for U.S. Appl. No. 14/180,564.
Office action dated Feb. 26, 2015 for U.S. Appl. No. 13/414,176.

(56) References Cited

OTHER PUBLICATIONS

Office action dated Mar. 4, 2016 for U.S. Appl. No. 13/874,046.
Office action dated Mar. 21, 2012 for U.S. Appl. No. 13/286,378.
Office action dated Mar. 21, 2014 for U.S. Appl. No. 13/414,176.
Office action dated Mar. 22, 2012 for U.S. Appl. No. 13/286,757.
Office action dated Apr. 7, 2015 for U.S. Appl. No. 13/685,909.
Office action dated May 2, 2012 for U.S. Appl. No. 13/096,602.
Office action dated May 3, 2016 for U.S. Appl. No. 13/665,160.
Office action dated May 11, 2016 for U.S. Appl. No. 15/081,595.
Office action dated May 12, 2016 for U.S. Appl. No. 15/081,550.
Office action dated May 26, 2016 for U.S. Appl. No. 15/081,526.
Office action dated May 31, 2016 for U.S. Appl. No. 15/096,083.
Office action dated Jun. 5, 2015 for U.S. Appl. No. 13/874,046.
Office action dated Jun. 17, 2014 for U.S. Appl. No. 13/414,176.
Office action dated Jun. 17, 2016 for U.S. Appl. No. 15/130,149.
Office action dated Jul. 23, 2012 for U.S. Appl. No. 13/286,378.
Office action dated Jul. 23, 2012 for U.S. Appl. No. 13/286,757.
Office action dated Aug. 18, 2014 for U.S. Appl. No. 14/180,564.
Office action dated Aug. 28, 2014 for U.S. Appl. No. 14/180,524.
Office action dated Sep. 19, 2014 for U.S. Appl. No. 13/685,909.
Office action dated Oct. 14, 2015 for U.S. Appl. No. 13/685,909.
Office action dated Oct. 23, 2015 for U.S. Appl. No. 13/665,160.
Office action dated Nov. 19, 2012 for U.S. Appl. No. 13/096,602.
Office action dated Dec. 29, 2014 for U.S. Appl. No. 13/685,909.
Co-pending U.S. Appl. No. 15/096,083, filed Apr. 11, 2016.
Co-pending U.S. Appl. No. 15/130,149, filed Apr. 15, 2016.
International search report and written opinion dated Aug. 30, 2016 for PCT/US2016/028297.
Co-pending U.S. Appl. No. 15/201,088, filed Jul. 1, 2016.
European search report and opinion dated Jul. 12, 2016 for EP Application No. 13851258.
Zip® Surgical Skin Closure. Fast, non-invasive alternative to staples, sutures and glue. Accessed Aug. 17, 2016. http://www.ziplinemedical.com/products/zip-surgical-skin-closure/.
European search report and opinion dated Feb. 7, 2017 for EP Application No. 140829202.
European search report with written opinion dated Jul. 12, 2016 for EP13851258.
International search report with written opinion dated Jul. 14, 2017 for PCT/US2017/027695.
International search report with written opinion dated Jul. 18, 2017 for PCT/US2017/028537.
International search report with written opinion dated Aug. 30, 2016 for PCT/US2016/028297.
Notice of allowance dated Feb. 21, 2017 for U.S. Appl. No. 14/625,366.
Notice of allowance dated Feb. 23, 2016 for U.S. Appl. No. 15/081,595.
Notice of allowance dated Sep. 30, 2016 for U.S. Appl. No. 15/130,149.
Notice of allowance dated Oct. 5, 2016 for U.S. Appl. No. 15/096,083.
Notice of allowance dated Oct. 14, 2016 for U.S. Appl. No. 15/081,550.
Notice of allowance dated Dec. 19, 2016 for U.S. Appl. No. 15/130,149.
"Office action dated Jun. 1, 2017 for U.S. Appl. No. 15/442,382.".
"Office action dated Jun. 2, 2017 for U.S. Appl. No. 13/665,160.".
Office action dated Nov. 17, 2016 for U.S. Appl. No. 15/081,595.
Office action dated Dec. 1, 2016 for U.S. Appl. No. 13/665,160.
dictionary.com definition of fixed, accessed on Sep. 13, 2017, http://www.dictionary.com/browse/fixed accessed on Sep. 13, 2017, http://www.dictionary.com/browse/fixed.
Extended European search report and opinion dated Jul. 27, 2017 for EP Application No. 15733186.
Merriam-webster definition of integral, accessed on Sep. 13, 2017, https://www.merriam-webster.com/dictionary/integral.
Office action dated Jul. 27, 2017 for U.S. Appl. No. 14/851,059.
Office action dated Aug. 24, 2017 for U.S. Appl. No. 14/958,803.
Office Action dated Sep. 22, 2017 for U.S. Appl. No. 13/665,160.
Office Action dated Sep. 26, 2017 for U.S. Appl. No. 13/685,909.
Office Action dated Oct. 5, 2017 for U.S. Appl. No. 14/958,818.
Office Action dated Nov. 28, 2017 for U.S. Appl. No. 15/442,382.
PCT/US2017/059286 International Search Report and Written Opinion dated Mar. 6, 2018.
U.S. Appl. No. 14/851,059 Notice of Allowance dated Mar. 14, 2018.
"Notice of Allowance dated Jun. 15, 2018 for U.S. Appl. No. 13/665,160.".
"Office action dated Jun. 6, 2018 for U.S. Appl. No. 15/201,088.".
"U.S. Appl. No. 14/958,803 Notice of Allowance dated Apr. 4, 2018".
U.S. Appl. No. 14/958,803 Notice of Allowance dated May 11, 2018.
"U.S. Appl. No. 13/685,909 Office Action dated May 1, 2018".

\* cited by examiner

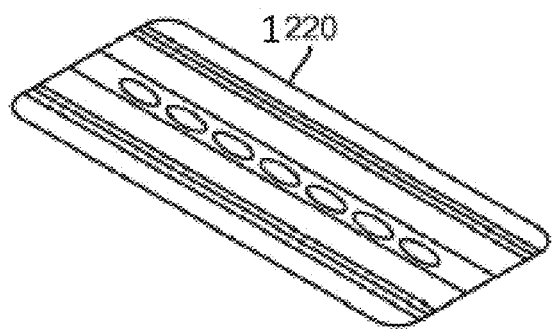
FIG. 1E1
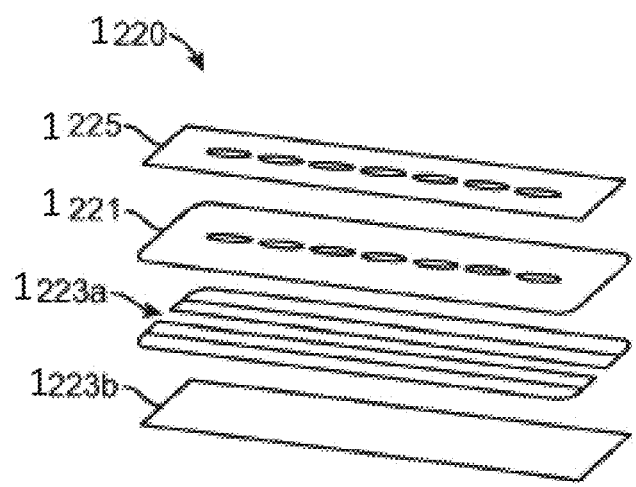
FIG. 1E2

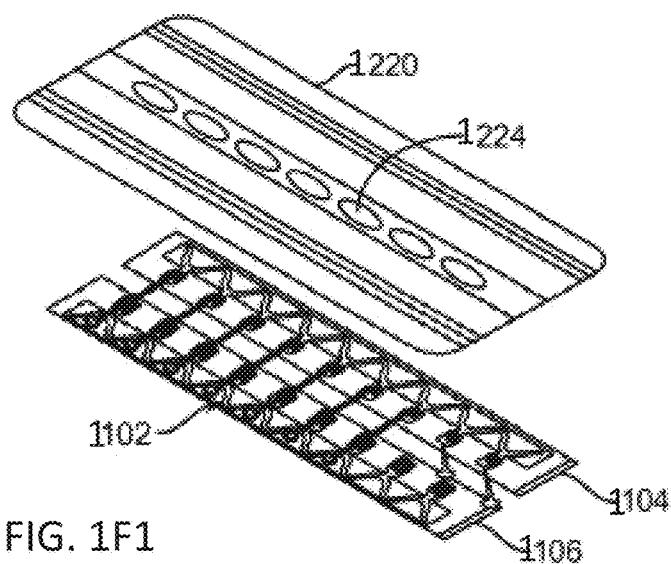
FIG. 1F1
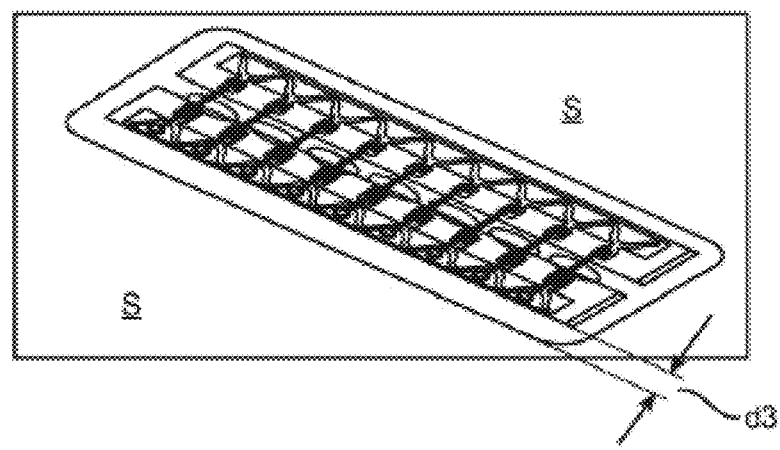
FIG. 1F2
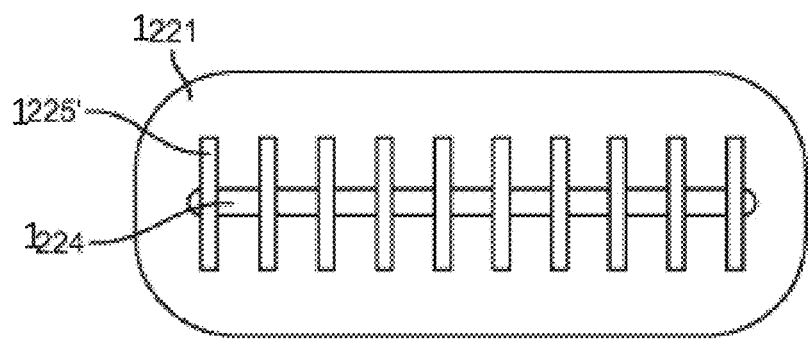
FIG. 1F3

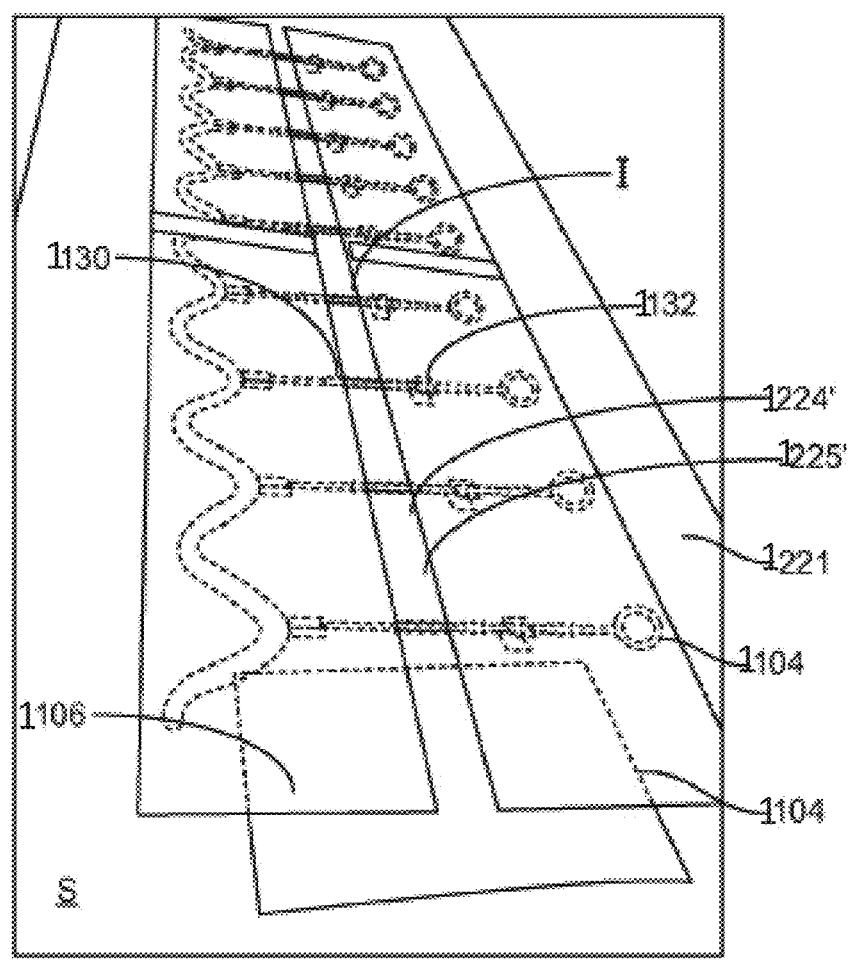
FIG. 1G1
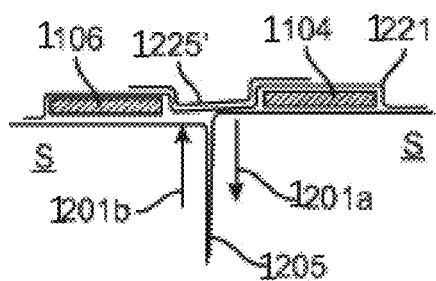
FIG. 1G2

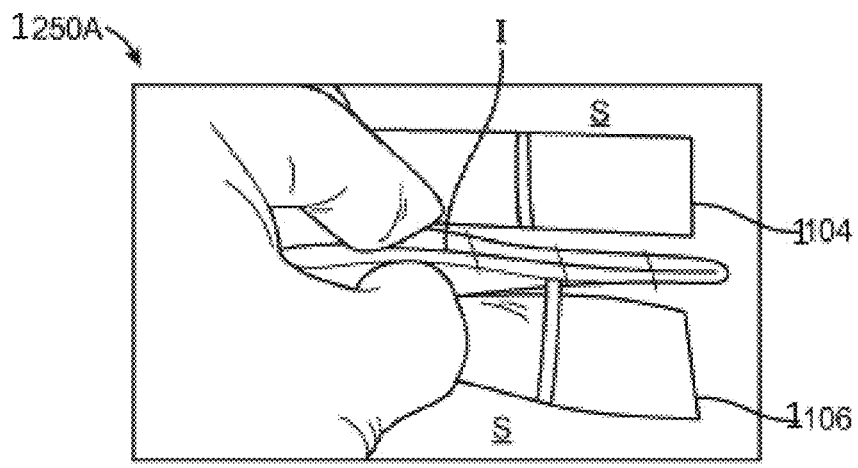
FIG. 1H1
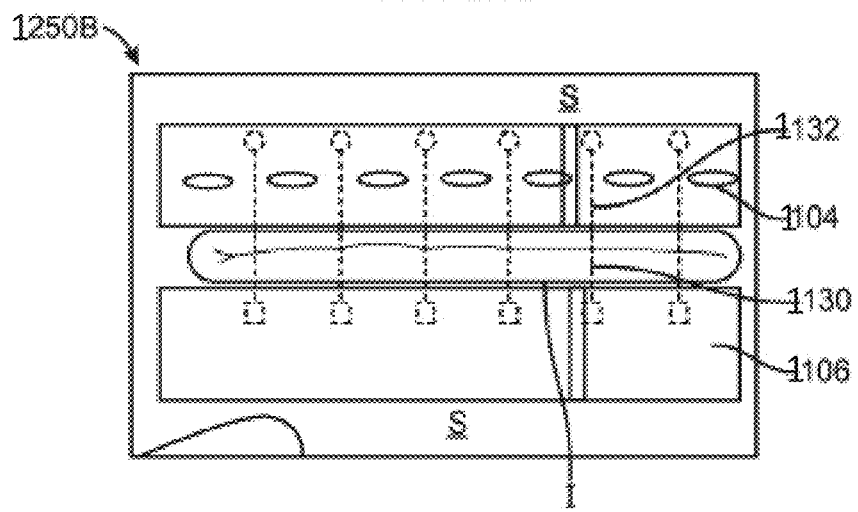
FIG. 1H2
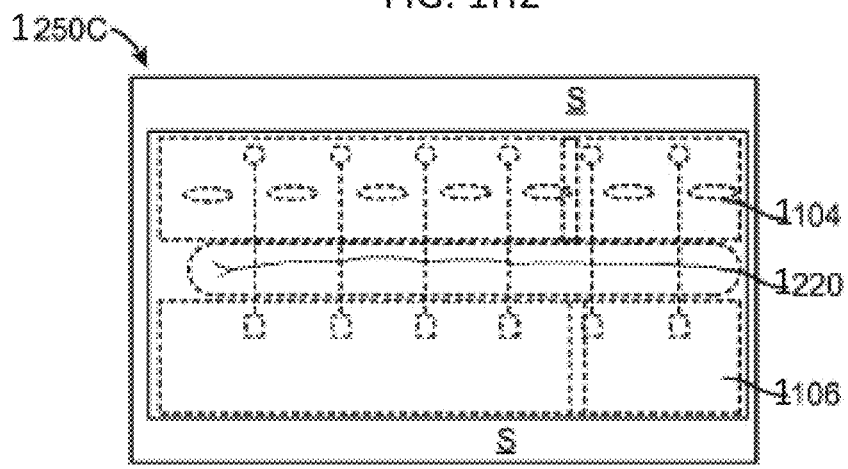
FIG. 1H3

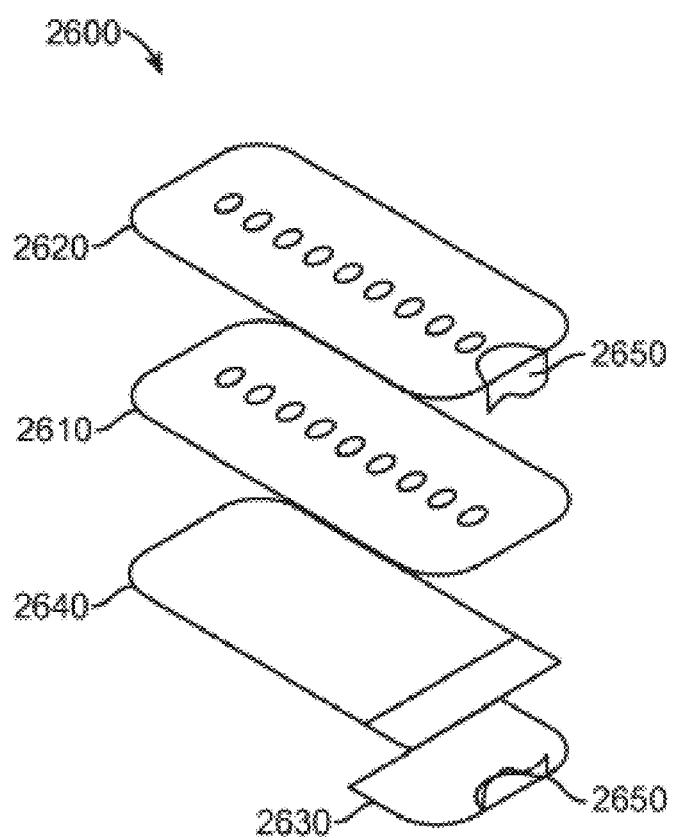
FIG. 1I1

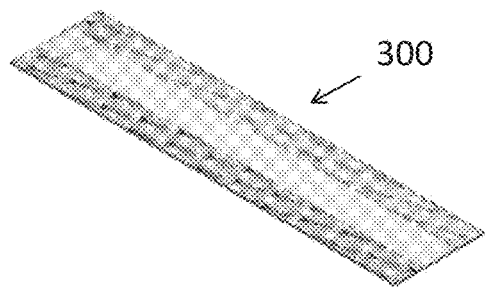
FIG. 4A
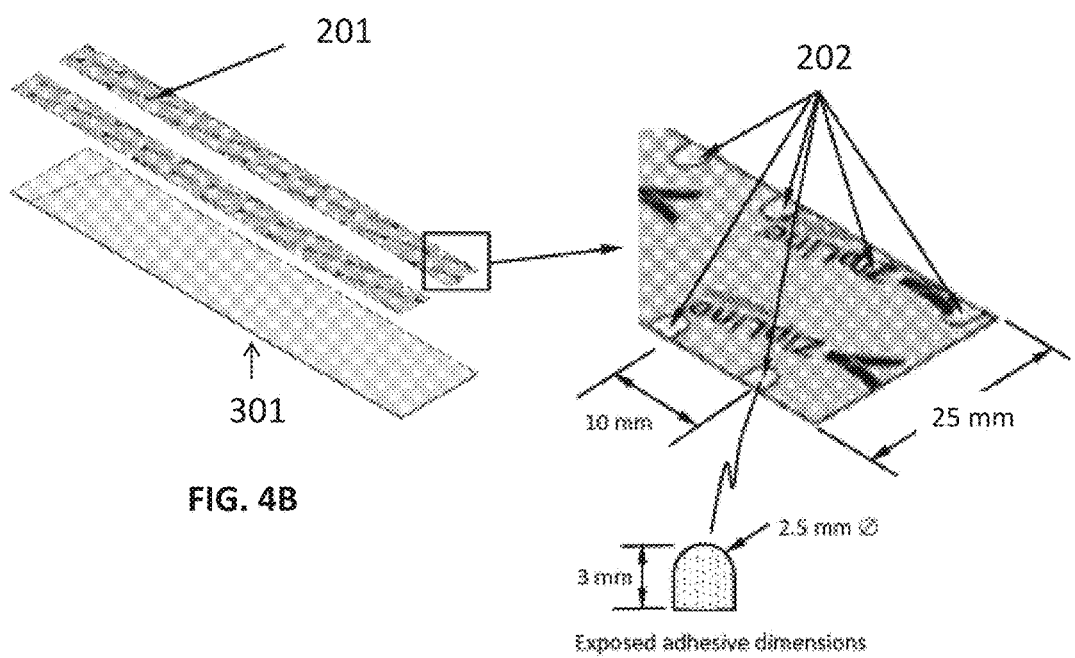
FIG. 4B
FIG. 4C

MEANS TO PREVENT WOUND DRESSINGS FROM ADHERING TO CLOSURE DEVICE

CROSS-REFERENCE

This application claims the benefit of U.S. Provisional Application No. 62/202,572, filed Aug. 7, 2015, which application is incorporated herein by reference.

The subject matter of this application is related to the subject matter of the following U.S. patents and U.S. patent applications: application Ser. No. 13/414,176, filed 7 Mar. 2012 and issued as U.S. Pat. No. 9,179,914 on 10 Nov. 2015; application Ser. No. 14/958,803, filed 3 Dec. 2015; application Ser. No. 14/958,818, filed 3 Dec. 2015; application Ser. No. 14/851,059, filed 11 Sep. 2015; application Serial No. 13/286,757, filed 1 Nov. 2011 and issued as U.S. Pat. No. 8,323,313 on 4 Dec. 2012; application Ser. No. 14/625,366, filed 18 Feb. 2015; application Ser. No. 13/665,160, filed 31 Oct. 2012; application Ser. No. 14/180,564, filed 14 Feb. 2014 and issues as U.S. Pat. No. 9,089,328 on 28 Jul. 2015; and application Ser. No. 14/180,524 filed 14 Feb. 2014 and issued as U.S. Pat. No. 9,050,086 on 9 Jun. 2015 which are incorporated herein by reference.

The subject matter of this application is related to the subject matter of the following PCT applications: application Serial No. PCT/US2010/000430, filed 3 May 2010; application Serial No. PCT/US2015/049671, filed 11 Sep. 2015; application Serial No. PCT/US2012/062820, filed 31 Oct. 2013; application Serial No. PCT/US2013/067563, filed 30 Oct. 2013; application Serial No. PCT/US2014/016587, filed 14 Feb. 2014; application Serial No. PCT/US2015/010188, filed 5 Jan. 2015; and application Serial No. PCT/US2015/028066, filed 28 Apr. 2015 which are incorporated herein by reference.

BACKGROUND

The present disclosure relates to medical devices, systems, and methods for wound closure. In particular, devices, systems, and methods for preventing undesired adherence of wound dressings to an applied closure device are disclosed.

Many surgical incision or wound closure devices comprise first and second base panels which are adhered to the skin on the two lateral sides adjacent the incision or wound. The base panels are then laterally coupled to one another (such as with tensioning elements) to close and maintain closure of the wound or incision. Such wound closure devices are disclosed by U.S. patent application Ser. No. 13/414,176 (U.S. Pat. No. 9,179,914), Ser. Nos. 14/958,803, 14/958,818, 14/851,059, 13/286,757 (U.S. Pat. No. 8,323,313), Ser. Nos. 14/625,366, 13/665,160, 14/180,564 (U.S. Pat. No. 9,089,328), and Ser. No. 14/180,524 (U.S. Pat. No. 9,050,086) and PCT application publication nos. PCT/US2010/000430, PCT/US2015/049671, PCT/US2012/062820, PCT/US2013/067563, PCT/US2014/016587, PCT/US2015/010188, and PCT/US2015/028066, which are incorporated herein by reference. Such closure devices are commercially available as the Zip® device available from Zipline Medical of Campbell, Calif.

After closure of the surgical incision or wound, many physicians, physician assistants, nurses, and other associate caregivers and medical professionals typically apply a wound dressing to the incision or wound. The purpose of the wound dressing use may vary, but can include any or all of the following: absorption of wound exudate, minimizing infection risk, protecting the wound during bathing and other patient activities, and preventing patient visualization and/or tampering with the wound site. Wound dressings may be applied immediately after surgical closure, or at any time during the post-surgical wound healing. Wound dressings may also be removed at any time during the post-surgical wound healing period, and replaced with a new dressing as needed.

Wound dressings can come in various shapes and configurations. One common dressing configuration is the "island dressing" which comprises of an absorbent central pad surrounded on all sides by a skin adhesive. Many commercially available dressings are available. Examples of dressing types desired for use with closure devices include, but are not limited to: Convatec Aquacel™ Ag, Smith & Nephew Opsite® Post-Op, Argentum Medical Silverlon®, and Mölnlycke Mepilex® Border.

Typically the central pad does not have a skin adhesive, though some brands (e.g., Mölnlycke Mepilex® dressings) provide a low-tack adhesive such as silicone, across the pad. Other dressings may comprise of a thin polyurethane-acrylic adhesive film laminate (e.g., 3M Tegaderm®) to cover and protect the wound. Dressings can also be fashioned by the user, such as by applying gauze or Telpha pads to the wound and securing them with tape or polyurethane-adhesive films. The wound dressing pad and/or adhesive itself may or may not incorporate anti-microbial substances such as silver, chlorhexidine, and others well-known in the art. Pressure sensitive adhesives are typically used for adherence of the dressing to the skin, with the most common being derived from acrylic, hydrocolloid, or silicone. Other skin adhesives may also be used that are readily available from commercial sources.

SUMMARY

Because many closure devices rely on adhesion to the skin to function, premature loss of adhesion can result in the wound not having sufficient closure force and/or isolation from distraction forces to ensure adequate healing. Wound dressings applied over such closure devices may contain skin adhesives that strongly adhere the wound dressing to the closure device. Removal of the wound dressing can result in the closure device being removed from the skin before the wound is fully healed. Accordingly, it is desired to discourage adherence of the wound dressing to closure devices.

The present disclosure relates to devices, systems, and methods for protecting closure devices from wound dressing adhesives. Protection of the outer perimeter of the closure device adhesive base panels (e.g., those laminated with a polyurethane or polyethylene film) to prevent peel initiation from the dressing is desired. In many embodiments, the entire panel is protected. Protection of the tensioning elements crossing the incision (e.g., molded straps and locks adhered to each panel) may be desirable, but may not be as critical since these elements are often located under the non-adhesive pad of the wound dressing.

Aspects of the present disclosure provide methods of closing an incision or wound. First and second base panels of a closure device may be provided. The first and second base panels may be configured to adhere to tissue adjacent first and second lateral sides, respectively, of the incision or wound. The closure device may be coated with a low friction or non-stick coating. A wound dressing may be positioned over the cured coating and the closure device, with the closure device being adhered to tissue. The cured coating may allow the wound dressing to be removed from the closure device while adherence of the first and second base panels with the tissue is maintained.

The low friction or non-stick coating may comprise a non-stick fluoropolymer coating. The low friction or non-stick coating may comprise a silicone compound, a silicone oil, or parylene. The closure device may be coated with the low friction or non-stick coating at a thickness of 0.25 to 5.0 microns. The low friction or non-stick coating may be cured at a temperature of no more than 60 C.°, and in some cases, no more than 45 C.°. The cured coating may remain bound to the closure device after the wound dressing is removed. The cured coating may be removed from the closure device concurrently with removal of the wound dressing. At least a portion of the closure device may be masked before coating the closure device with the low friction or non-stick coating. For instance, areas of the left and right base panels where adhesive of the panels are exposed may be masked. The low friction or non-stick coating may comprise an anti-microbial coating. The cured coating may be stretchable.

Aspects of the present disclosure may also provide methods of closing an incision or wound. First and second base panels of a closure device may be adhered to tissue adjacent first and second lateral sides, respectively, of the incision or wound. First and second sacrificial cover strips may be positioned over the first and second base panels that are adhered to the tissue. The first and second sacrificial cover strips may be adhered to the first and second base panels, respectively. A wound dressing may be positioned over the first and second sacrificial cover strips that are adhered to the first and second base panels. The wound dressing may adhere to the first and second sacrificial cover strips. The first and second sacrificial covers may allow the wound dressing to be removed while leaving the closure device adhered to the tissue.

To position the first and second sacrificial cover strips over the first and second base panels, perimeters of the first and second sacrificial cover strips may be extended over perimeters of the first and second base panels, respectively. One or more of the first or second sacrificial cover strips may overlap full lengths of one or more of the first or second base panels, respectively. The first and second sacrificial strips may comprise upper adhesive surfaces having a first adhesive tack and lower adhesive surfaces having a second adhesive stack less than the first adhesive tack.

One or more of the first or second sacrificial cover strips may comprise one or more perforations, notches, or cutout spaces. One or more of the first or second sacrificial cover strips may comprise a polyurethane film layer. One or more of the first or second sacrificial cover strips may comprise a pressure sensitive adhesive layer. A release liner may be removed from the first and second cover strips prior to the first and second cover strips being adhered to the first and second base panels.

Aspects of the present disclosure provide systems for closing an incision or wound. The system may comprise a closure device and a sacrificial cover strip. The closure device may comprise first and second adherent base panels and a plurality of closure components to couple the first and second adherent base panels to one another. The sacrificial cover strip may comprise first and second sacrificial cover strips having an adherent bottom surface and a release liner coupled thereto.

The perimeters of the first and second sacrificial cover strips may be greater than perimeters of the first and second adherent base panels such that when adhered thereto, the first and second sacrificial cover strips can extend beyond the perimeters of the first and second adherent base panels, respectively. The full lengths of the first and second sacrificial cover strips may be greater than the full lengths of the first and second adherent base panels such that when adhered thereto, the first and second sacrificial cover strips can overlap the full lengths of the first and second adherent base panels, respectively.

One or more of the first or second sacrificial cover strips may comprise one or more perforations, notches, or cutout spaces. One or more of the first or second sacrificial cover strips may comprise a pressure sensitive adhesive layer. The first and second sacrificial cover strips may comprise adherent upper surfaces having a first adhesive tack, and the adherent bottom surfaces of the first and second sacrificial cover strips may comprise a second adhesive tack less than the first adhesive tack. The first and second sacrificial cover strips may each comprise a first polyurethane layer, a second polyurethane layer, and a pressure sensitive adhesive layer therebetween.

The closure device may be coated with a low friction or non-stick coating that may be cured onto at least a portion of the closure device as described above and herein.

Aspects of the present disclosure provide devices for covering an incision or wound closure device adhered to skin adjacent a wound or incision. An exemplary device may comprise a strip, a support film, and a release liner. The strip may be configured for placement over the closure device previously adhered to the skin adjacent the wound or incision. The support film may back the strip. The release liner may be releasably attached to a bottom surface of the strip. The bottom surface of the strip may be adhesive. The support film may comprise an absorbent material for absorbing exudate from the incision or wound. The strip may be porous. The support film may comprise an adhesive bottom surface. The support film may extend beyond the perimeter of the strip. The strip may comprise comprises a first portion and a second portion separable from one another.

Aspects of the present disclosure may provide methods of closing an incision or wound. First and second base panels of a closure device may be provided. The first and second base panels may be configured to adhere to tissue adjacent first and lateral sides, respectively, of the incision or wound. A wound dressing may be positioned over the closure device and incision or wound. The wound dressing may absorb exudate generated from the incision or wound between the first and second base panels. The wound dressing may comprise an absorbent material and a support film extending over the perimeter of the absorbent material. A portion of the support film extending over the perimeter of the absorbent material may be adhesive. The wound dressing may comprise a cover strip coupled to the absorbent material and support film. The cover strip may be porous. A release liner may be removed from the wound dressing prior to the wound dressing being positioned over the closure device and incision or wound.

Aspects of the present disclosure may provide systems for closing an incision or wound. The system may comprise a closure device and a wound dressing. The closure device may comprise first and second base panels configured to adhere to tissue adjacent first and second sides, respectively, of the incision or wound. The first and second panels may be releasably and adjustably attached to one another. The wound dressing may be configured to extend over the first and second base panels to adhere to the tissue adjacent the first and second sides of the incision or wound, thereby covering the closure device and incision or wound. The wound dressing may be configured to be peeled off the tissue without removing the first and second base panels adhered to the first and second sides, respectively, of the incision or wound. The wound dressing may comprise an adhesive peripheral portion and an absorbent inner portion. The absorbent inner portion may be configured to be positioned over the incision or wound when the wound dressing is adhered to the tissue adjacent the first and second sides of the incision or wound to absorb exudate therefrom. The wound dressing may comprise a releasable liner releasably adhered to a bottom surface of the wound dressing. The wound dressing may comprise first and second parts axially separable from one another.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 1E1 shows a perspective view of a cover for the incision closure appliances, according to many embodiments.

FIG. 1E2 shows an exploded view of the cover of FIG. 1E1.

FIG. 1F1 shows an exploded view of an incision closure appliance assembly comprising the incision closure appliance of FIG. 1D and the cover of FIG. 1E1, according to many embodiments.

FIG. 1F2 shows a perspective view of the incision closure appliance assembly of FIG. 1F1 adhered onto the skin of a patient, according to many embodiments.

FIG. 1F3 shows a top view of the elastomeric reinforcement layer of the cover of FIG. 1E1.

FIG. 1G1 shows a perspective view of the incision closure appliance assembly of FIG. 1F1 adhered onto the skin of a patient in accordance with the principles of the present disclosure.

FIG. 1G2 shows a sectional schematic diagram of the incision closure appliance of FIG. 1F1 adhered onto the skin of a patient, according to many embodiments.

FIGS. 1H1, 1H2, and 1H3 illustrate a method of applying the incision closure appliance assembly of FIG. 1F1 on the skin of a patient, according to many embodiments.

FIGS. 1I1, 1I2, 1I3, 1I4, and 1I5 illustrate embodiments of a cover for wound dressings and incision closure appliances, according to many embodiments.

FIG. 2 shows a perspective view of a closure device similar to that in FIG. 1C provided with sacrificial cover strips and additionally a magnified view showing lateral notches of the sacrificial cover strip, according to embodiments of the present disclosure.

FIG. 4A shows a perspective view of a closure device and sacrificial cover strip assembly, according to many embodiments.

FIG. 4B shows an exploded view of the closure device and sacrificial cover strip assembly of FIG. 4A.

FIG. 4C shows a magnified view of the closure device and sacrificial cover strip assembly of FIG. 4A showing lateral notches of the sacrificial cover strip, according to embodiments of the present disclosure.

FIG. 5 shows an exploded view of the closure device and sacrificial cover strip assembly of FIG. 4, including views of the different layers of the sacrificial cover strips.

DETAILED DESCRIPTION

The apparatus and methods of the present disclosure can be used during both the formation and the closure of surgical incisions made to a patient's skin or other tissue during surgical procedures or wounds in general. As described hereinafter, the direction of the incision or wound will define both "axial" and "lateral" directions as those terms are used herein. Most incisions will be made along a generally straight line which will define the axial direction. The lateral direction will generally be across the axial direction, typically but not necessarily being perpendicular or normal to the axial direction. Most incisions will be generally linear but in some cases the incisions could be curved or have other geometries. The term "axial" will then apply to the direction of the incision at any particular location, resulting in lateral directions which could also vary.

Figure 1A:
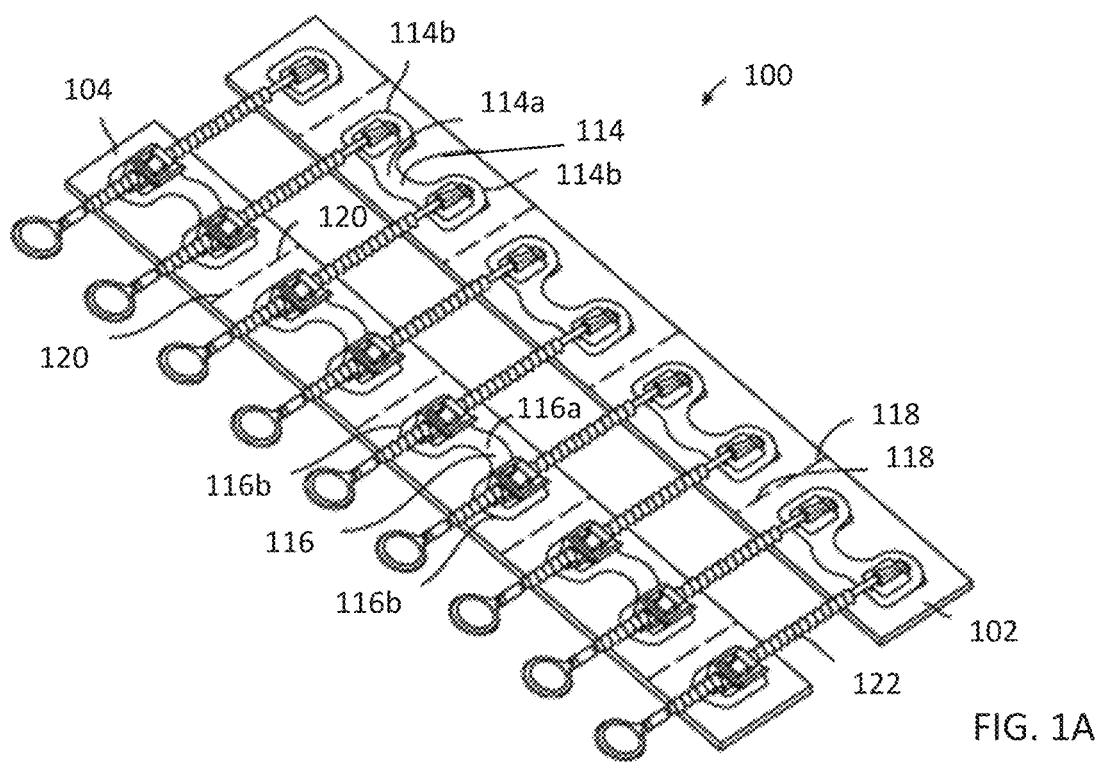
FIG. 1A shows a perspective view of a surgical incision or wound closure device, according to many embodiments.
Figure 1B:
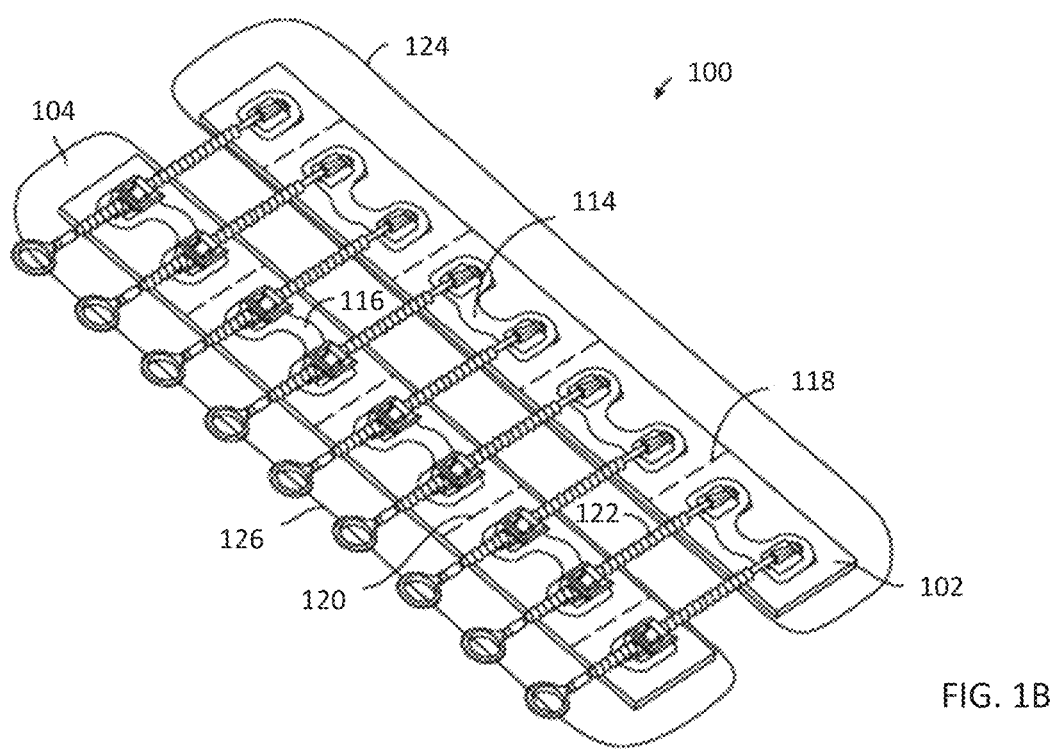
FIG. 1B shows a perspective view of the closure device of FIG. 1A provided with additional lateral skirts, according to many embodiments.
Figure 1C:
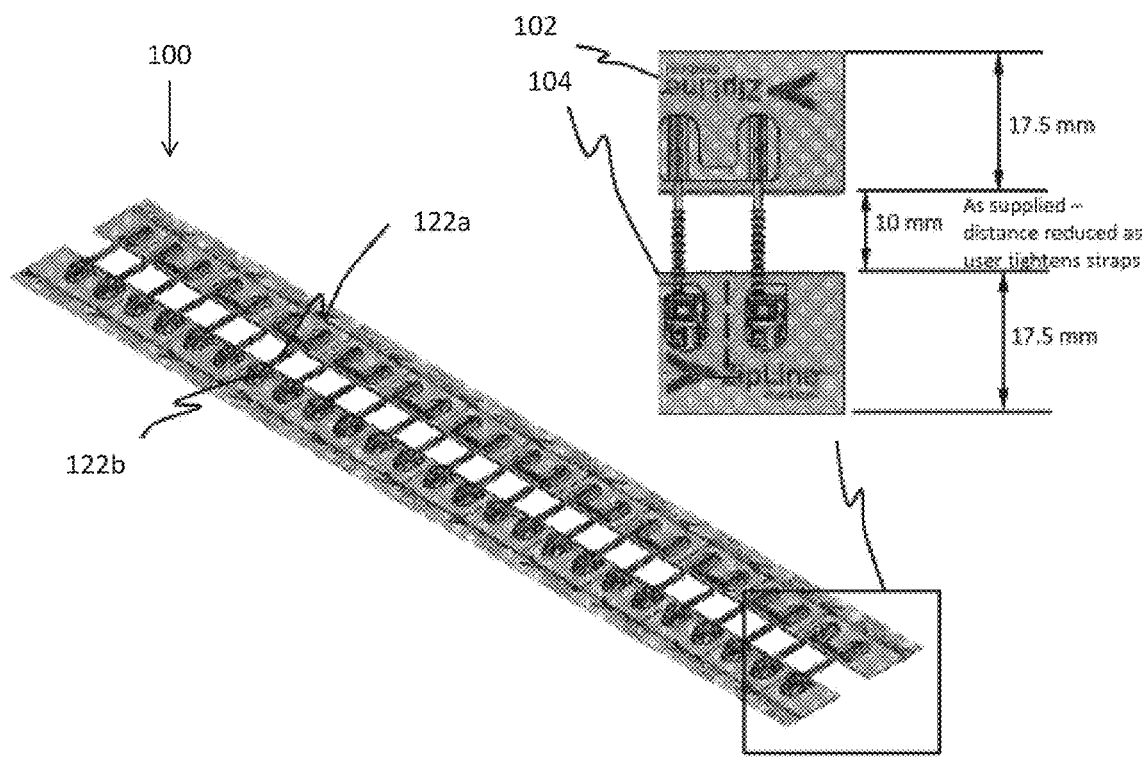
FIG. 1C shows a perspective view of an elongated closure device similar to that in FIG. 1A and additionally a magnified view showing its lateral tie assemblies.

Referring now to FIGS. 1A-1C, a closure device 100 usable with embodiments of the present disclosure is shown. The closure device or base assembly 100 may comprise a right base panel 102 and a left base panel 104. The right base panel 102 may comprise an upper layer 106 and a lower layer 108. Similarly, the left base panel 104 may comprise an upper layer 110 and a lower layer 112. The upper layers 106, 110 will typically be flexible but stiff enough securely close tissue and minimize disruption of the incision and surrounding tissue. The upper layers 106, 110 may comprise a plastic layer made of rubber, latex, polyurethane, silicone, a thermoplastic elastomer, a woven fabric, a spun fabric, or similar materials. The adhesive bottom layers 108, 112 will typically be flexible and more elastic than the upper layers 106, 110 to follow any movement of the underlying skin and tissue to maintain adhesion, minimize blistering, and otherwise reduce irritation. The adhesive bottom layers 108, 112 may comprise a hydrophilic adhesive material such as a hydrocolloid, a hydrogel, an acrylic polymer, poly (ethylene glycol), and the like.

The right and left base panels 102, 104 may comprise structures to facilitate and limit axial and lateral stretching of the base assembly 100. These structures may also evenly distribute the closure force exerted on an incision and may be disposed on the base assembly 100 along its axial length. The right base panel 102 may comprise one or more right force distribution structures or axial supports 114. Each right axial support 114 may comprise an axial support portion or spine 114a and two lateral support portions 114b coupled to the axial ends of the spine 114a. Together, the spine 114a and the two lateral support portions 114b form a C-shape which in some embodiments can open axially to a degree to facilitate axial stretching of the right base panel 102 between two laterally adjacent lateral support portions 114b of adjacent supports 114 while limiting the axial stretching between the two lateral support portions 114b of a single support 114. In many embodiments, the C-shaped axial support 114 is only flexible enough to allow flexing vertically but is stiff to minimize axial and lateral stretching. The right axial supports 114 may be outward facing which may help to distribute any mechanical load against the tissue closure to the incision between the right and left base panels 102, 104. Similarly, the left base panel 104 may comprise one or more left force distribution structures or axial supports 116. Each left axial support 116 may comprise an axial support portion or spine 116a and two lateral support portions 116b coupled to the axial ends of the spine 116a. Together, the spine 116a and the two lateral support portions 116b form a C-shape which in some embodiments can open axially to a degree to facilitate axial stretching of the left base panel 102 between two laterally adjacent lateral support portions 116b of adjacent supports 116 while limiting the axial stretching between the two lateral support portions 116b of a single support 116. In many embodiments, the C-shaped axial support 116 is only flexible enough to allow flexing vertically but is stiff to minimize axial and lateral stretching. The left axial supports 116 may be outward facing which may help to distribute any mechanical load against the tissue closure to the incision between the right and left base panels 102, 104.

As shown in FIG. 1B, the base panel assembly 100 may further comprise skirts 124 and 126. The skirts 124, 126 may be similar to the thin base assembly covers described below. For example, each skirt 124, 126 may comprise a 0.001 inch thick urethane film coupled to a 0.002 inch thick acrylic adhesive. The adhesive may be applied to the whole under-surface of the skirts 124, 126 or may just to the region of the skirts 124, 126 beyond the base panels 102 or 104. During construction of the base panel assembly 100, the skirts 124, 126 may be applied directly over all or a portion of the adhesive layers 108, 112, respectively. The skirts 124, 126 may be applied in place of, or in addition to, the thin film upper layers 106, 110, respectively. Release liners as described herein may further be provided to line the adhesive under-surface of the skirts 124, 126. The skirts 124, 126 may extend beyond the outer border of the base panels 102, 104, respectively, by 8 mm or in a range of 1 to 20 mm, for example, but does not span across the lateral area between the base panels 102, 104 to improve the ability to visualize and/or clean the incision site. Thus, the skirts 124, 126 may help provide additional adhesive support and/or creep reduction to the adhesive layers 108, 112 of the base panels 102, 104 without having to align and place a separate cover or cover sheet over the base panel assembly 100. After manufacturing, the skirts 124, 126 are typically already precisely aligned relative to the base panels 102, 104. A separate cover or cover sheet as described herein may still be used to prevent tampering of the incision site and components of the base panel assembly 100. As the skirts 124, 126 already laterally extend over the base panels 102, 104, respectively, such a separate cover or cover sheet may not require precise placement relative to the base panel assembly 100 and could be more narrow compared with other covers or cover sheets described herein.

One or more perforations 118 may be provided in-between axially adjacent right axial supports 114 on right panel 102 to facilitate the axial and/or lateral stretching of the right base panel 102. The perforations 118 may be all the way through the upper and lower layers 106, 108 to provide aeration to the underlying tissue or may only be present on the upper layer 106. Similarly, one or more perforations 120 may be provided in-between axially adjacent left axial supports 116 on left panel 104 to facilitate the axial and/or lateral stretching of the base panel 102. The perforations 120 may be all the way through the upper and lower layers 110, 112 to provide aeration to the underlying tissue or may only be present on the upper layer 110. There may only be a single perforation 118 or 120 between the axial supports 114 or 118. There may be a plurality of perforations 118 or 120 in a lateral line between the axial supports 114 or 118. The perforations 118, 120 may also reduce the stress incurred as the skin stretches radially outward from the incision such as during joint articulation and swelling.

A plurality of perforations 118, 120 may, for example, be provided in-between the axial ends of the right and/or left axial supports 114, 116. A plurality of axially-aligned perforations may be provided such that at least the upper and lower layers 110, 112 of the base panels 102, 104, respectively, may break into separate segments when axially stretched. In some instances, during the wear duration of the device 100, the perforations 118, 120 may allow the layers 106 and 108 of right panel 102 and the layers 110 and 112 of left panel 104 to completely divide and separate at the perforation line. The ability to completely divide and separate further allows the skin to stretch axially as needed, with the elongation allowed (and limited) by the linkages of axial supports 114 and 116 and closure components 122 discussed below. As discussed herein, a flexible, compliant cover may be applied over the base panels 102, 104 after the incision is closed. The cover may further serve to provide (and limit) axial and lateral movement of the base structure 100. Alternatively or in combination, one or more of the right or left base panels 102, 104 may be laterally cut and separated in-between the force distribution structures or axial supports 114, 116 to facilitate the axial and/or lateral stretching of the right and/or left base panels 102, 104.

To couple the right and left base panels 102, 104 laterally together and optionally to tighten the right and left base panels 102, 104 against one another, the base assembly 100 may further comprise a plurality lateral closure components or tie assemblies 122. The lateral closure components or tie assemblies 122 may comprise a ratchet mechanism. The lateral tie assemblies 122 may couple laterally adjacent right and left axial supports 114, 116 together, typically at their axial ends. As shown in FIGS. 1A-1C, the placement of the right and left axial supports 114, 116 on the right and left panels 102, 104, respectively, may be staggered or axially offset, and the right and left axial supports 114, 116 may be C-shaped structures with lateral end portions 114b, 116b that laterally face and align with one another (and are connected to one another by a lateral tie assembly 122). For example, the far end lateral portion 114b of a first right axial support 114 may be laterally aligned with the near end lateral portion 116b of a first left axial support 116, the far end lateral portion 116b of the first left axial support 116 may be laterally aligned with the near end lateral portion 114b of a second right axial support 114, and so forth. Thus, the lateral tie assemblies 122 and right and left axial supports 114, 116 may be connected to one another to form a line of consecutive lateral tie assemblies 122 and right and left axial supports 114, 116, and this line may have a serpentine arrangement that laterally spans the right and left base panels 102, 104 (i.e., goes across the distance between the right and left base panels 102, 104) as shown in FIGS. 1A-1C. The serpentine arrangement of lateral tie assemblies 122 and right and left axial supports 114, 116 may one or more of evenly distribute the closure forces provided by the base assembly 100 on an incision, provide (and limit) axial flexibility of the base assembly 100, and provide rigidity or stiffness to the base assemblies 100 to sufficiently close an incision and allow it to heal with minimized disruption and distension (i.e., provide lateral and axial stability). In many embodiments, the lateral supports 114, 116 are stiff so that the areas of the base panels 102, 104 that are not covered with the lateral supports 114, 116 stretch. Because these uncovered areas are offset from one another from the right base panel 102 to the left base panel 104, the tie assemblies 122 may pivot axially from their anchor points as the incision is axially stretched. Such axial pivoting of the tie assemblies 122 may bring the left and right panels 102, 104 closer together to maintain the closure of the incision.

The material of the lateral tie assemblies 122 and the right and left axial supports 114, 116 may include, for example, a flexible, resilient plastic, typically a hard plastic, such as Nylon, Polypropylene, Polyethylene, Poly carbonate, and other thermoplastic polymers. Often, the lateral tie assemblies 122 and the right and left axial supports 114, 116 may comprise a material less elastic than that of the right and left base panels 102, 104. Thus, greater stiffness (and less elasticity) may be provided toward the top of base assemblies 100. In other words, there may be an elasticity gradient between the top and bottom of the base assemblies 100. The tops of the base assembly 100 may be sufficiently rigid or stiff so that the incision closure appliance, when applied to an incision and surrounding tissue, prevents movement of tissue laterally adjacent the appliance to not substantially distend the covered incision and surrounding tissue. That is, movement of at least a portion of the applied incision closure appliance (e.g., a portion below the more stiff layers) is collective and does not disrupt the underlying incision. And, the bottom of the base assembly 100 may be sufficiently elastic such that blistering and adhesion loss due to movement of tissue adjacent the applied incision closure appliance are minimized. While a primary function of lateral tie assemblies 122 may be to apply tension to each base panel 102, 104 to hold the incision closed, in many embodiments, the lateral tie assemblies 122 may also serve to provide columnar strength so as to isolate the incision by minimizing effects of compression on (or bending/creasing along) the incision from distraction forces that could disrupt the incision edge alignment and apposition. The axial spacing, material property, and dimension of the lateral ties 122 may be optimized for sufficient axial bending flexibility and lateral compression and bending support. In preferred embodiments, the spacing between ties 122 is 10 mm, the material of the ties 1422 is nylon, and the dimension is a round cross-section of 0.030 inch.

The base assembly 100 may be placed over an incision in the skin of a patient or subject's joint, such as the knee, for example. In incisions placed in proximity to articulating joints, the knee in particular, closure device or closure appliance integrity is often challenged by a number of factors. These factors include longitudinal elongation, circumferential swelling, opening of the wound as articulation occurs, skin damage such as blistering, adhesion loss, and passage of wound exudates. Joints such as knee, elbow, ankle, and shoulder may undergo a movement which can sometimes result in articulation covering more than 135° movements, leading to the challenges noted above.

In a bent position, the skin around the knee can stretch up to 50% axially (i.e., parallel to the incision) and laterally (i.e., transverse or perpendicular to the incision). An incision closure appliance adhered to the skin in this area may preferably be able to provide enough tension to close the incision yet accommodate the stretch with minimal local stress. Minimizing the local stress may prevent local skin adhesion loss or damage to the skin if the adhesive loss does not occur. An important property for many incision closure appliances disclosed herein is the ability of the tension load of the appliance's closure elements to be distributed across an area larger than that of the tension element attachment point itself. Furthermore, the structure comprising the adhesive to which the tensioning elements are attached may in many cases have the ability to distribute the compliance of the structure across the region of skin stretch such that the appliance holds the incision in place while the skin moves around it. Embodiments described herein may include a composite design of non-stretching tension elements (commonly referred to as "straps") that are linked to "locks" that hold the straps in place. For example, such elements may include the lateral tie assemblies 122 described above. These elements may be mounted over skin adhesives with elastic polymeric materials that help distribute the tension load. Such elastic polymers may in many cases have high elongation before yielding or permanently deforming and may include thermoplastic elastomers such as polyurethane as well as various grades of silicone. Such materials may also be easily formed into thin films necessary for maintaining a low profile and sufficient compliance.

The skin adhesive used in the appliance may also need to withstand the elongation of the skin and be able to retract/recoil when the skin is returned to an un-stretched condition (e.g., in the fully extended knee position). Hydrocolloid adhesives may provide such properties and may be preferably suited for this application. Other adhesives such as acrylic may also be used to provide this property. In general, such adhesives may need to be attached to an elastic thin film such as that described above in order to hold their structure during expansion and recoil. Without such support, the adhesive may tear and separate with repeated elongation.

Incision closure appliances constructed as a sequence of short segments may accommodate higher overall elongation without loss of adhesion or skin damage. Each individual segment may be subjected to the local stretching of the skin under it. The space between two adjacent segments may act as stress relieving space allowing the skin to stretch in that space. The segmentation may be achieved in number of ways: (1) by laying down individual segments along the incision line, or (2) allowing the device to divide into short segments as it is applied to the skin or after applying to the skin.

A preferred means of achieving segmentation after application to the skin comprises creating perforations (e.g., a lateral line of perforations to facilitate tearing) in the polyurethane layer (i.e., the upper layer 106, 110 of a base panel 102, 104) and leaving the underlying adhesive intact. The perforations may result in tearing of at least the upper layers (e.g., upper layers 106, 110) of the base panels along the perforated lines (e.g., lines 124, 126) when it undergoes stretching as the knee flexes (i.e., is articulated). In preferred embodiments, the adhesive panel on each side of the incision may be 12 mm wide, and the perforations within a given panel are spaced about 12-20 mm apart. Experimentation was performed and showed that a perforation of 3 mm cut and 1 mm tie distances are effective in achieving segmentation in 0.001 inch thick urethane base panels when the knee flexes. As the knee flexes, the skin may elongate in axial (along the incision) and lateral directions up to 50% in some locations. Separation of the polyurethane can thus relieve stress in the device as it undergoes stretch.

As an example, a surgically repaired knee may be inflamed for a number of days, which may result in approximately 30% radial swelling of the joint after closure. Elastic materials like polyurethane may allow the incision closure appliance to expand with this circumferential swelling. Minimizing the width of the appliance (e.g., 12 mm or less for each base panel segment 102, 104) may minimize the amount of the appliance subject to expansion in a direction perpendicular to the incision, and may thus preserve adhesion while minimizing potential for skin damage. Perforations in adhesive segments running in the lateral direction to the incision along lines may allow the base panels to stretch more easily axially. Perforations or other fenestrations could also be made near the outer edges of the adhesive segments parallel to the incision in order to reduce the stress incurred as the skin stretches radially outward from the incision such as during articulation and swelling.

Perforated segments of base panel upper layers, typically comprising polyurethane, may be held together with a continuous layer of the adhesive bottom layer, typically comprising a hydrocolloid adhesive, to allow laying down on the skin in one continuous motion. The incision closure appliances 100 may be provided with such a continuous adhesive bottom layer.

The base assembly or base panels of the incision closure appliances described herein preferably may be covered with a flexible adhesive film material at the end of a wound or incision closure. This film area preferably may be larger than the base incision closure panel elements such that it overlaps the elements onto the skin. The film may help prevent migration of the base and may prevent any accidental movements of the anchors and locking mechanisms. The cover film may be made from stretchable materials like rubber, latex, polyurethane, silicone or thermoplastic elastomer, etc. In preferred embodiments, a thin cover (e.g., laminate of 0.001" urethane and 0.002" thick acrylic adhesive), will have a greater compliance than the composite structure of the base panel elements. As a result, the cover may offer some strain relief between the exposed skin and the base segments. The cover may also be transparent to allow visual inspection of the incision. The cover may completely seal across the incision (e.g., as a barrier to infection) or there may be openings in the cover that are aligned with the incision line to allow passage of any exudates from the wound. The cover may also serve to improve the apposition of the incision edges by bridging the base panels and adhering to the skin edges between the base strips. The cover may also be constructed with additional reinforcing elements that improve the tensile strength between the base panel elements but allow for compliance along the incision length. A preferred embodiment may comprise a series of polyethylene adhesive tape strips applied to the cover.

While the user may apply the cover after the base assembly and panels are placed on the skin, it is also conceived that the cover material may be supplied as a "skirt" extending around the outer perimeter of the base segments. Thus, alignment of the cover materials relative to the base may not be dependent on the user placement. These same cover materials may provide the effects of preventing exposure of the hydrocolloid adhesive to patient clothing, limitation of migration of the hydrocolloid or other adhesive lower layer, providing strain relief for the tension on the base segments, etc.

In many embodiments, a hydrocolloid adhesive is used for tensioning skin for incision closure. The hydrocolloid may be prevented from creep by one or more of (1) using a laminate on the surface to limit creep or (2) applying an adhesive cover across the skin and the hydrocolloid adhesive to prevent creep and to provide strain relief to the skin to prevent skin damage.

In many embodiments, a cover as used with the base assembly may include one or more of perforations or openings to allow removal of wound exudate (as well as any applied bandages/absorbent material) without removal of the adhered base assembly.

In many embodiments, the cover comprises a composite of flexible urethane and reinforced strips. The composite construction may provide strength across the incision as well as provide for compliance along the incision length.

In many embodiments, the cover in combination with the base assembly aligns the skin incision edges or significantly prevents subsequent misalignment of the skin edges, in both the axial and lateral directions.

In many embodiments, cover liner configurations are provided such that part of the cover can be applied to the skin first, which then aids in the removal of other liners and thus may help control the thin materials so they lay out evenly with minimal wrinkling.

In many embodiments, the removal of a first liner may allow visualization during placement and may prevent the remainder of the device from sticking to the user.

The skin adhesive used for each panel 104, 106 may preferably comprise a hydrocolloid adhesive. Alternatively or in combination, the skin adhesive may comprise one of many acrylic formulations known in the art. Hydrocolloid adhesives may have the benefit of being very tacky and able to absorb moisture and shedding skin cells. Thus, hydrocolloid adhesives may be particularly suited for long-term wear applications (e.g., up to 14 days). In at least some instances, the hydrocolloid structure may be soft, however, and may be prone to creep under tension unless reinforced in some manner such as by covering the hydrocolloid adhesive layer with stiffer base panels 102, 104 or other covering structures disclosed herein.

Figure 1D:
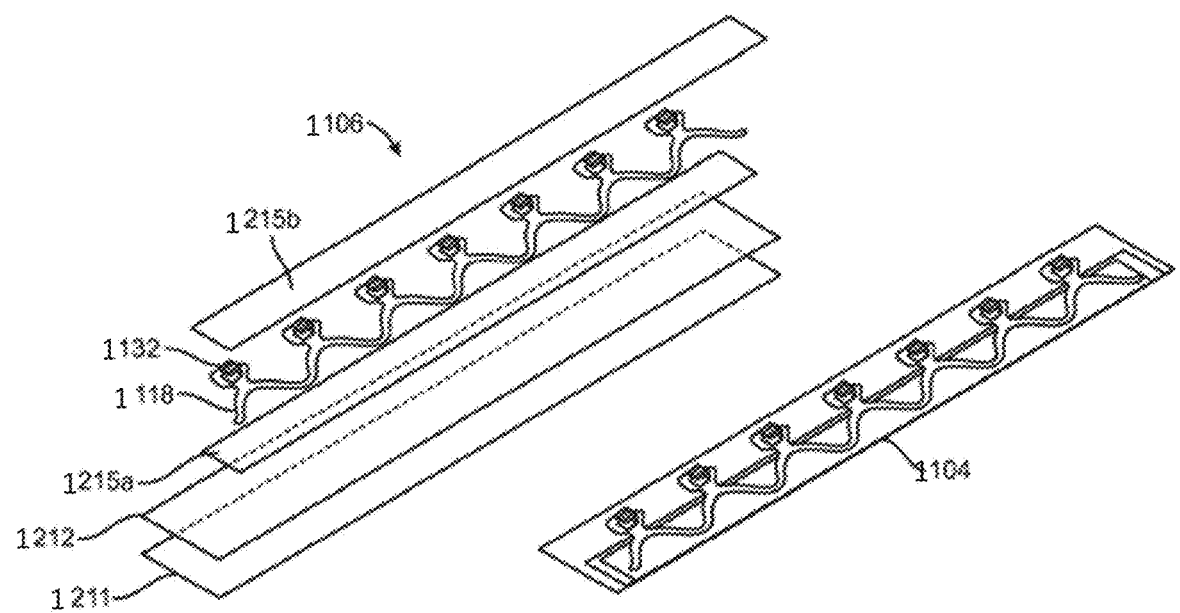
FIG. 1D shows an exploded view of a portion of an incision closure appliance, according to many embodiments.
Figure 112:
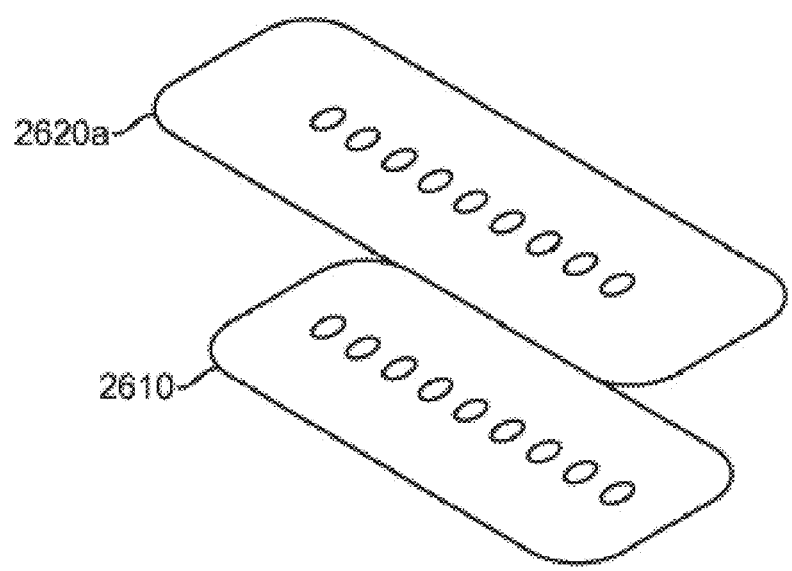
Figure 113:
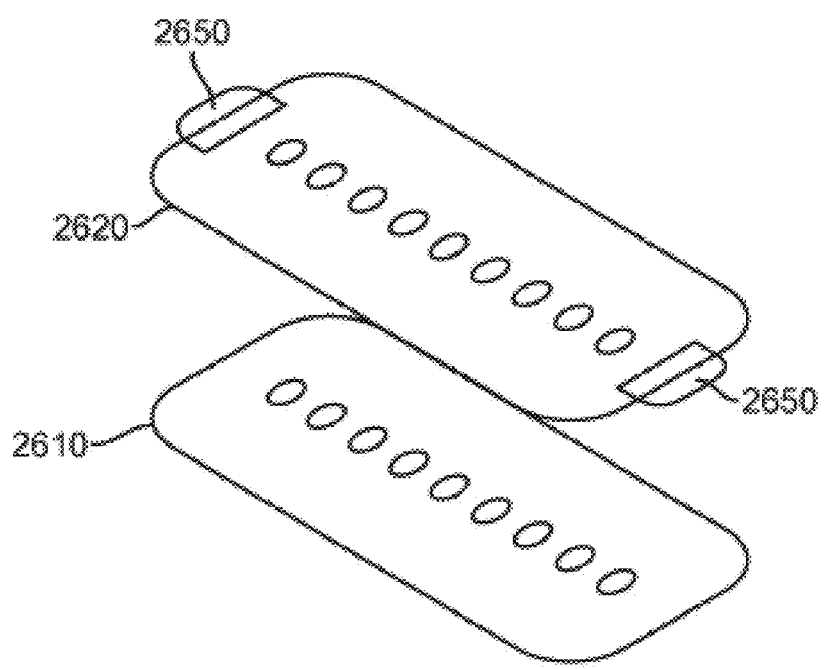
Figure 114:
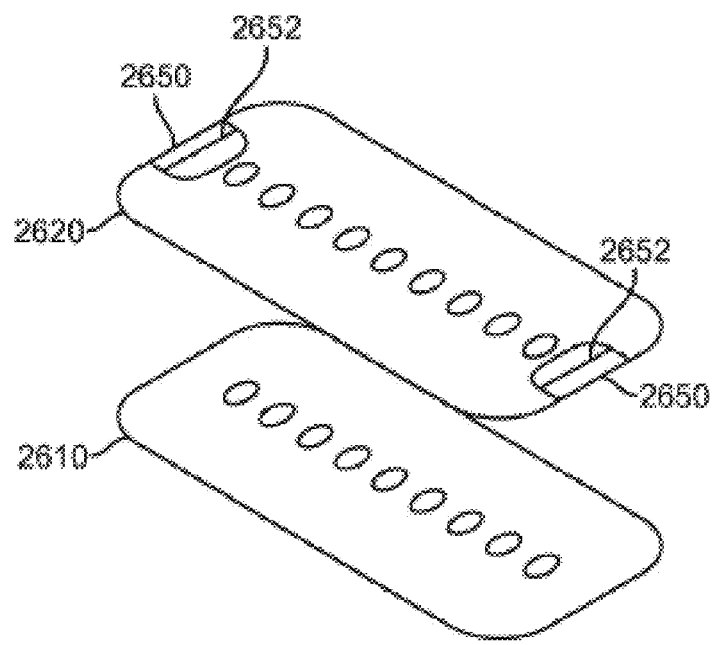
Figure 115:
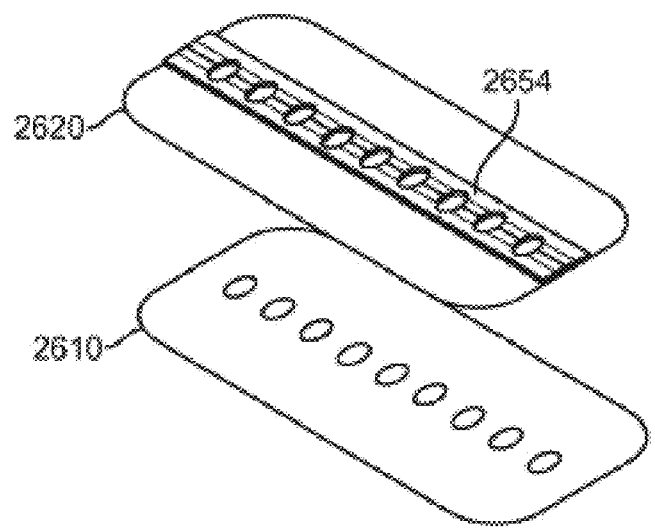

Accordingly, a further aspect of the present disclosure also provides various means of reinforcing and protecting the adhesive layer in the base assemblies of the incision closure appliances described herein as well as additional means of holding the skin edges together, particularly in the axial direction. In at least some cases, the hydrocolloid adhesive alone has very low tensile strength and may require a means of reinforcement to prevent it from tearing or creeping during use. As illustrated in FIG. 1D, an adhesive layer 1211 used in base panels 1104, 1106 of a closure device may be laminated with a thin layer of a compliant plastic or polymer 1212, such as urethane, preferably 0.001 inch thick, with a potential range up to 0.010" thick, that may help to maintain its structure during clinical use. The adhesive layer itself may nominally be 0.010 inch thick, but may range between 0.005 inch and 0.020 inch thick. Because tensioning elements comprising straps 1130 or locks 1132 attached to a load distribution component 1118 may be mounted to the top of the adhesive structure 1211, the possibility exists that the material could creep over time. The laminate 1212, as well as any other adhesive laminates 1215a, 1215b between the adhesive layer 1211 and the load distribution component 1118, may help provide the structure to prevent creep of the adhesive layer.

Figure 2:
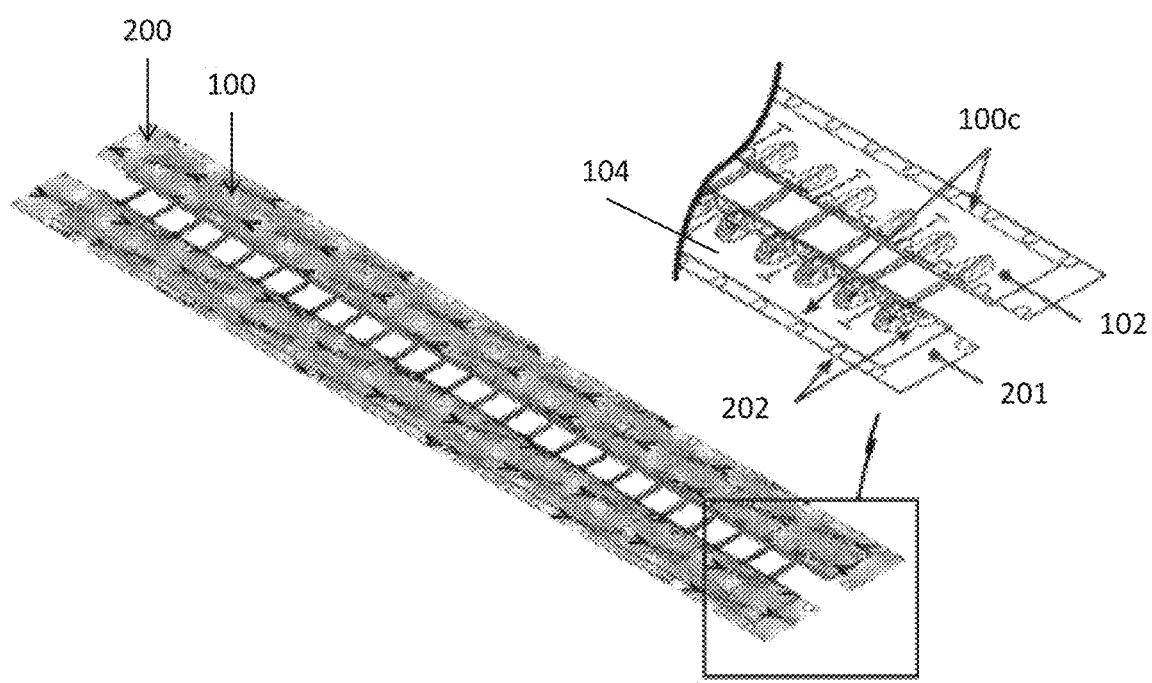

To further prevent migration of the adhesive panel 1211, a cover 1220 may also be applied over the panels 1104, 1106 as shown in FIG. 1E1. As shown in FIG. 1E2, the cover 1220 may comprise a thin, adhesive coated compliant elastomer 1221. In many embodiments, the cover 1220 further comprises a thin urethane layer (preferably 0.001 inch thick) coated with a skin adhesive, such as an acrylic adhesive (preferably 0.002 inch thick), which may be provided on one or more release liners 1223a, 1223b. The cover may further comprise reinforcing features 1225.

As shown in FIGS. 1F1 and 1F2, the cover 1220 may be constructed such that it may extend beyond the base panels 1104, 1106, thereby bridging a distance, d3, between the skin S and the panels 1104, 1106. A typical minimum necessary distance, d3, may be 8 mm but could range 2-15 mm. Besides helping prevent creep of the adhesive layer of the base panels 1104, 1106, the urethane skin adhesive of the cover 1220 may also help to strain relieve the tension applied to the base panels 1104, 1106 from movement of the surrounding skin S. This may serve to prevent skin damage (e.g., from erosion or blistering) at the base panel 1104, 1106 edges. It should be noted, however, that the compliant nature of the hydrocolloid offers local protection from blistering by itself being able to move with the skin S and thus resist damage to the skin S. In many embodiments, even with stiffer structures mounted to the outer surface of the adhesive layers, the compliance within the nominal 0.010" thickness of the adhesive layers down to the skin surface may provide resistance to skin damage.

Besides stabilizing and strain relieving the base panel structures, the cover 1220 may serve other purposes. By covering the location where a strap 1130 would engages a lock 1132, the cover 1220 may prevent the patient from tampering with the locks 1132 to the point where the straps 1130 could be disengaged. As shown in FIGS. 1F1-1F2, the cover 1220 may be fitted with openings 1224, 1224' along the length of the region overlapping an incision, such that externally applied gauze may absorb wound exudate. In other embodiments, the cover 1220 may not have openings in order to protect the wound from sources of infection. The cover 1220 itself may have reinforcing features 1225, 1225' to provide the base 1102 with additional resistance to the incision opening, particularly in regions between the straps 1130. FIG. 1F3 shows a particular embodiment where the reinforcing features 1225' could be rectangular strips of adhesive tape. The tape 1225' may preferably be stiffer perpendicular to the skin incision than the surrounding compliant urethane layer 1221. The tape 1225' may be constructed from any combination of adhesive coated woven fabric, polymer fibers, polyethylene, polypropylene, nylon, PET, hydrocolloid, or other materials known in the art. The reinforcing features 1225' may also add "body" or stiffness to the cover 1220 to aid in its placement. The urethane layer 1210 may be constructed of such materials to give it a bi-directional stretch.

The spacing of the reinforcing features 1225, 1225' may be important to ensure the longitudinal (parallel to the incision line) compliance of the cover 1220 (e.g., due to the compliant thin urethane). This may serve to improve patient comfort and the resistance to skin damage by allowing the cover 1220 and the underlying base assembly 1102 to move with motions of the body. This effect may be from the cover 1220 alone or as a composite effect with features on the base assembly 1102 which may allow longitudinal compliance. The reinforcements 1225, 1225' may also be of a uniform construct, but perforated, slit, or otherwise mechanically interrupted to allow stretch and/or controlled tearing with body motion. The thin urethane layer(s) of the cover 1220 may also be mechanically interrupted to the same effect. In at least some cases, the reinforcing features 1225, 1225' of the cover 1220 may not extend the entire width (perpendicular to incision) of the cover 1220. This limited covering width may help ensure strain relief to the body motion away from the base assembly 1102 perpendicular to the incision I. In preferred embodiments, the region of the cover 1220 reinforced by the reinforcement members 1225, 1225' extends 10 mm in each direction away from the incision edge, but this may range from 2-50 mm.

Another feature of the cover 1220 may be to be able to add control to the incision edge, particularly between the tensioning elements 1130, 1132 of the base assembly. As illustrated in FIG. 1G1, the tensioning elements 1130, 1132 combined with the base panels 1104, 1106 may serve to approximate the incision edges 1205 together. Once the skin S is approximated, it may be important that the skin edges be aligned vertically (perpendicular to the skin surface). Vertical misalignment may lead to slower healing and visible "step-off", or ledge, in the incision that may result in poor scar cosmesis. By having portions of the cover 1220 adhere to each edge of the base panels 1104, 1106 along the incision, each edge may held under tension in vertical alignment as shown by arrows 1201a, 1201b. Adhesive on portions of the cover 1220 crossing the incision I may also adhere directly to the skin S at the incision edge, further shortening the distance between the adhered incision edges and further enhancing vertical skin alignment. In preferred embodiments, the portions of the cover 1220 crossing the incision I are rectangular strips 1225' of adhesive tape as shown in FIG. 1F3. The width of each strip 1225' and the axial gap between the strips 1225' may be optimized for incision edge control, incision visibility, and the escape of wound exudate. A preferred embodiment may comprise a strip 12 mm wide and spaced 6 mm apart, with the straps located between each strip. Other widths and spacing are also contemplated. By not bridging/tenting over each strap 1130, the strip 1225 may lay flatter against the skin S for better adhesion and edge control.

In some embodiments, the reinforcing features 225, 225' may be constructed to limit the amount of bending at the incision site. The reinforcing features 225, 225' in these embodiments may be stiffer than the skin S, and preferably stiffer than the surrounding elements of the base panels 104, 106. In this way, and bending or compression of the skin S through normal patient motion would be isolated, or the propagation limited, around the incision site. While this motion isolation or limitation would help strengthen the incision site in tension, a greater benefit may be to prevent the incision edges from significantly or unevenly inverting, everting, or shifting in a direction perpendicular to the skin surface. Reinforcing materials discussed above may be used, with the thickness tailored to create the desired stiffness. Preferably, the composite of the base assembly 102 and cover 220 may be constructed to create a smooth transition in stiffness and compliance from the surrounding skin to the isolated incision site.

In particular methods of use, after initial closure of the incision using the base assembly 1102 to approximate the skin edges, the base panels 1104, 1106 may be pushed together further to "pooch" the closed incision I upward to slightly evert the edges and/or compress the skin S around the incision edges to relieve tension. FIGS. 1H1-1H3 illustrate an embodiment of this method in an in-vivo tissue model. FIG. 1H1 shows a step 1250A in which the base panels 1104, 1106 are adhered to the skin S adjacent an incision I and are pushed together to "pooch" the closed incision I upward. The base panels 1104, 1106 may be then pulled together further to hold the tissue in this orientation. These methods may be enhanced by positioning the base panels 1104, 1106 away from the incision edge by 5-10 mm. In a step 1250B shown by FIG. 1H2, the base panels 1104, 1106 may be locked in place relative to one another with the straps 1130 and the locks 1132. In a step 1250C shown by FIG. 1H3, the cover 1220 may then be applied to lock in the relative location of the base panels 1104, 1106 and "pooched" incision I. The incision I could be further reinforced with the reinforcing elements 1225, 1225' discussed above.

A given cover 1220 may in many embodiments be fitted with release liners to aid in user handling of the cover 1220 before and during application to the patient. As shown in FIGS. 1E1 and 1E2, the cover 1220 may have release liners 1223a, 1223b applied in a three-part configuration. The user may first remove a longitudinal center liner 1223b to apply the center exposed adhesive to the base assembly 1102 and skin incision region. Removal of this liner 1223b first, in combination with visualization through the clear plastic and/or openings in the center of the base 1220, may allow the user to see the base assembly 1102 underneath such that the cover 1220 can be properly aligned with the base assembly 1102 as the cover 1220 is applied. This may also help provide regions of the cover 1220 that do not stick to the user until the cover 1220 is initially secured to the base assembly 1102 and/or the skin S. Next, the side release liners 1223a may be removed in a direction perpendicular to the incision I. The liners 1223a hold and tension the very thin urethane to keep it from substantially wrinkling as it is applied to the skin S. Also, by sticking the center of the cover 1220 to the base assembly 1102 and/or the skin S first, the cover 1220 may be held in place such that sufficient tension and control may be applied to the side release liners 1223a for smooth application of the remainder of thin adhesive coated cover 1220 to the patient. Alternatively or in combination, the liners may be constructed such that the first liner is removed to expose a narrow strip over the full width of the cover 1220 (perpendicular to the incision I) to allow initial placement on the base assembly 1102 and/or skin S, followed by removal of one or two additional liners in a direction parallel to the incision I. The first liner may be in the middle of the length, on either end, or somewhere in between. If not on the end, two additional liners may be required, each removed in a direction from the location of the first liner outward along the length of the device. If the first liner was on one end, a second single liner may be removed from the location of the first liner out toward the end of the device.

Another release liner configuration may be to have a single liner which could be completely removed from the bottom of the cover 1220 before application. This type of liner may require an outer film, or casting sheet, be lightly adhered to the outer surface of the cover 1220 to help the thin urethane hold its shape and provide the user with locations at the sides and/or ends which do not have adhesive and thus would not stick to the user's hands during application. The outer film could be over the entire outer surface or just a particular width surrounding the perimeter of the cover 1220. The film and/or the release liner could also have an area extending beyond that of the thin urethane in the cover 1220. Once the cover adhesive is attached to the base assembly 1102 or skin S, the casting sheet may be easily removed from the outside of the cover 1220.

As described herein, flexible wound dressings and wound or incision closure devices or appliances are typically flexible and stretchable to follow the contour of curved parts of the body (e.g., arm, longer incisions that are curvilinear, etc.) or the areas that undergo stretching (e.g., knee). To assist the draping of such devices, a backing material may be used which assists in maintaining the dressing shape during the application. Such temporary backing material described herein may have a number of advantages. The backing material may be clear to enable the visual of the wound. The material may be non-stretchable to prevent elongation of the dressing or closure device or appliance during application. The backing may be easily removable after the application of the wound dressing or closure device or appliance so as to not affect the adhesion of the actual dressing on the wound site. The backing material may also assist in the handling of the dressing during manufacturing process. In many embodiments, the backing material may couple to a dressing or closure device with peel-off release liners on the adhesive side of the dressing to enable easy and reliable removal of the backing material.

Referring now to FIG. 1I1, a wound dressing cover 2600 may comprise a flexible sheet 2610 made of a flexible material like rubber, urethane, silicone, etc. The flexible material 2610 may be laminated on a relatively stiffer material in the form of a casting sheet or carrier layer 2620. The casting sheet 2620 prevents the flexible material 2610 from rolling onto itself and becoming unusable. The flexible sheet 2610 may have an adhesive on one side (e.g., the bottom side) and a relatively rigid (stiff) carrier layer or casting sheet 2620 on the other side. The adhesive side is protected by two liners 2630, 2640 that can be sequentially removed to expose the adhesive in a controlled manner. To apply the dressing 2600 on the wound or incision, a small strip of adhesive is exposed by removing one of the release liners, usually the smaller release liner 2630. This release liner 2630 may be attached to the casting sheet 2620 using a tape 2650. The exposed part of the flexible sheet 2610 may then be adhered at one end of the wound or incision. The flexible cover 2600 then follows the contour of the wound or incision and the curvature on the body as the second release liner 2640 is slowly removed to expose the adhesive sequentially.

The first release liner 2630 which is typically still attached to the casting sheet 2620 with the tape 2650 may then be used to lift the casting sheet 2620 from the flexible dressing 2610.

A manufacturing process for the wound dressing cover 2600 and associated liners 2630, 2640 may be to use a single die to cut a common profile (perimeter) of the laminate of the release liners 2630, 2640, the flexible dressing (with adhesive) 2610, and the casting sheet 2620. Upon removal of the liners 2630, 2640 and application of the dressing sheet 2610 to the skin, the casting sheet 2620 may remain on the dressing sheet 2610. Removal of the casting sheet 2620 may require initiation by delaminating and peeling back an edge of the casting sheet 2620 from the dressing sheet 2610. Once initiated, the continued peel and removal of the casting sheet 2620 may be straightforward. Initiation and lift of the edge of the casting sheet 2620 may not always be intuitive and may requires a free edge connected to the casting sheet 2620 to help identify the lift point and begin the peel. The tape 2650 may be used to bridge the casting sheet 2620 to the release liner 2630 and may provide an easily identifiable tab which can be used to initiate the peel.

Figure 5:
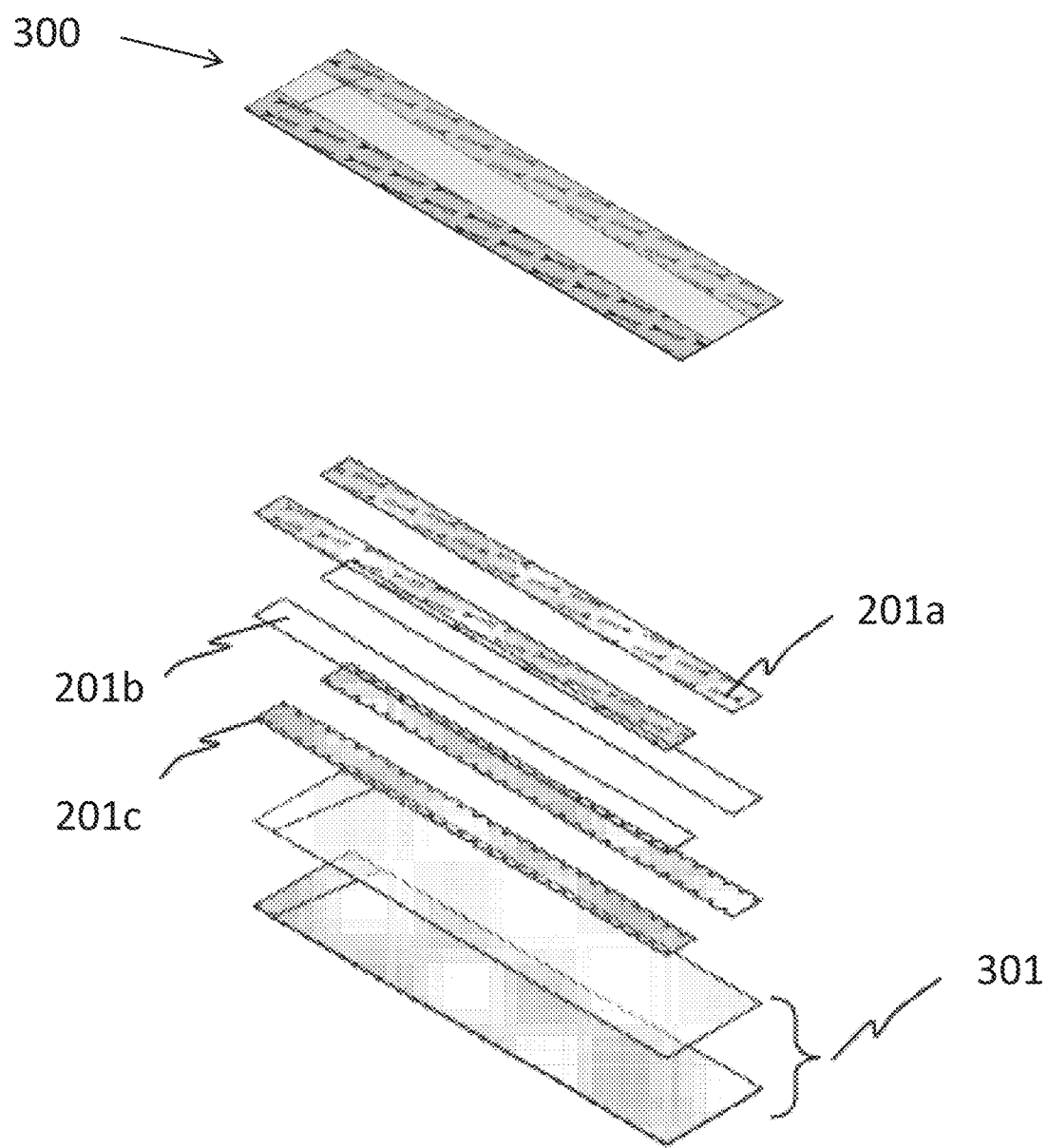

Alternative configurations of the casting sheet 2620 may be used to initiate the peel of the casting sheet 2620 as shown in FIGS. 1I2-1I5.

As shown in FIG. 1I2, the casting sheet die may be cut such that the casting sheet 2620a extends axially beyond the flexible dressing sheet 2610 (e.g., the liners 2630, 2640 and urethane material of the flexible dressing sheet 2610 may be "kiss cut" to the surface of the casting sheet 2620a).

As shown in FIG. 1I3, the casting sheet 2620 may have tape 2650 applied to either one or both axial sides to extend beyond the casting sheet. The tape 2650 may not necessarily be attached to the release liner 2630.

As shown in FIG. 1I4, casting sheet tape 2650 may be attached at or near the axial edge(s) of the casting sheet 2620 and also extends inside the profile of the casting sheet 2620, with a loose non-adherent edge 2652 for the user to grasp.

As shown in FIG. 1I5, the casting sheet die may be cut (e.g., kiss cut such that the casting sheet 2620 is not cut into the flexible dressing sheet 2610) from one axial edge to a partial or full-length distance to another axial edge of the casting sheet 2620. The cut casting sheet 2620 may be separated with a "pinch" by the user to create an edge to grasp. The interior die cut edge may also have a tape or similar tab 2654 applied to one or both of the interior edges to grasp and peel as shown in FIG. 1I5.

In many embodiments, the casting sheet 2620, 2620a and/or tape 2650, 2652, 2654 may be of a different color or have markings to distinguish from the flexible dressing sheet 2610 and release liners 2630, 2640.

One or more of the components of the incision closure appliances or incision closure appliance assemblies disclosed herein, including one or more of the various base assemblies, base panels, force distribution structures, axial supports, lateral supports, closure components, tie assemblies, straps, locks, adhesive layers, adhesive layers, covers, cover structures, drapes, etc., may be comprised of, be coated with, or otherwise incorporate one or more of an antifungal, antibacterial, antimicrobial, antiseptic, or medicated material. For example, such materials may be incorporated into the hydrocolloid adhesive layer, as another layer or coating between the skin and the adhesive layer (covering at least a portion of the adhesive layer), incorporated into the base assembly cover or at least its adhesive layer, etc. One or more wells, grooves, openings, pores, or similar structures may be provided on the device or apparatus components to facilitate such incorporation. In many embodiments, such materials may comprise one or more of silver, iodide, zinc, chlorine, copper, or natural materials such as tea tree oil as the active agent. Examples of such antifungal, antibacterial, antiseptic, or medicated materials include, but are not limited to, the Acti-coat™. family of materials available from Smith & Nephew plc of the U.K., the Acticoat™ Moisture Control family of materials available from Smith & Nephew plc of the U.K., the Contreet™ Foam family of materials available from Coloplast A/S of Denmark, the UrgoCell™ Silver family of materials available from Urgo Limited of the U.K. (a subsidiary of Laboratoires URGO of France), the Contreet™ Hydrocolloid family of materials available from Smith & Nephew plc of the U.K., the Aquacel™ Ag family of materials available from ConvaTec Inc. of Skillman, N.J., the Silvercel™ family of materials available from Kinetic Concepts, Inc. of San Antonio, Tex., Actisorb™ Silver 220 available from Kinetic Concepts, Inc. of San Antonio, Tex., the Urgotul™ SSD family of materials available from Urgo Limited of the U.K. (a subsidiary of Laboratoires URGO of France), the Inadine™ family of materials available from Kinetic Concepts, Inc. of San Antonio, Tex., the Iodoflex™ family of materials available from Smith & Nephew plc of the U.K., the Sorbsan Silver™ family of materials available from Aspen Medical Europe Ltd. of the U.K., the Polymem Silver™ family of materials available from Ferris Mfg. Corp. of Burr Ridge, Ill., the Promogram™ family of materials available from Kinetic Concepts, Inc. of San Antonio, Tex., the Promogram Prisma™ family of materials available from Kinetic Concepts, Inc. of San Antonio, Tex., and the Arglaes™ family of materials available from Medline Industries, Inc. of Mundelein, Ill. Components of the closure devices described in commonly owned U.S. Pat. Nos. 8,313,508, 8,323,313, and 8,439,945; U.S. Patent Publication No. 2013/0066365; and PCT application nos. US 2010/000430, US 2011/139912, US 2011/40213, US 2011/34649, and US 2013/067024 and others incorporated herein may also be comprised of, be coated with, or otherwise incorporate one or more of an antifungal, antibacterial, antimicrobial, antiseptic, or medicated material, including but not limited to one or more of the materials listed above.

In many embodiments, topical medicinal agents are incorporated directly into the wound closure appliances described herein. Because a wound closure device is often applied in close proximity to a wound or incision in need of medicinal protection, the incorporation of such medicines directly into the closure device may be beneficial. In wounds at risk of infection, incorporation of anti-microbial agents may be beneficial, for example. Anti-microbial agents may include antibiotic medicines as well as antiseptic metal ions and associated compounds which may include silver, iodine, copper, and chlorine, or natural materials such as tea tree oil. In wounds prone to fungus, medicinal agents such as zinc may be warranted, for example. Combinations of any of these agents may also be of benefit and thus may be incorporated into wound closure appliances.

Topical medicinal agents may be incorporated into the closure devices in a way to give the closure devices the ability to wick exudate away from the wound (e.g., to direct unwanted organisms away from the wound and/or prevent skin maceration), while keeping the wound sufficiently hydrated for improved healing.

Coatings.

According to further aspects of the present disclosure, after assembly of a closure device (such as closure device 100) a coating can be applied to the outer surface to prevent adhesion to the wound dressing. An exemplary coating may utilize a non-stick fluoropolymer coating applied and cured to the device 100, typically with a process that does not require temperatures exceeding 60° C. for 5 min., and more preferably under 45° C. for any period of time. The adherence of the coating with the polyurethane film of the wound closure device may be most desired, though protection of all external surfaces may be desirable as well. The fluoropolymer film thickness may range from 0.25 to 5.0 microns, preferably about 1-3 microns. Coating would typically take place with release liners or other suitable material in contact with the skin adhesive surface to prevent contamination of the skin adhesive with the coating. Such a coating would typically be applied as part of the manufacturing process such that no additional coating is required to be applied by the user. However, in other embodiments, just before dressing application, the user may instead apply a preferably sterile oil-based liquid or gel to the outside of the Zip device to prevent adhesion. Examples include petrolatum and silicone oil.

Other coatings that do not require cure temperatures that can damage the device adhesives (typically above 60° C.) may be applied. These may include silicone compounds or oils (cured to the material or uncured), parylene, and other coatings well-known in the art. The coating may preferably remain bound to the closure device upon removal of the dressing, though could also act by deadening the applied adhesive, and/or acting as a sacrificial layer that is pulled up with the dressing instead of the underlying device. Sacrificial coatings may be thicker, more in the range of 0.0005"-0.010".

While preferable to apply to the entire finished device, the coating could be applied to selective regions of the device by masking areas to not be coated. This may be useful if coating is incorporated into an intermediary process where component bonding must be subsequently performed to non-coated regions of the device, or if coating of other components (e.g., the locks and straps) results in undesirable low friction (e.g., straps don't stay engaged in locks or strap slips out of user's hands). In other cases, the coating may be on a material that is applied separately to the device (e.g., a strip of polyurethane film). This may be useful if the coating process requires an elevated temperature or use of solvents that are incompatible with the rest of the device.

In other embodiments, the coating material may have an antimicrobial compound incorporated into the coating. The coatings described above are preferably conformal to the device surfaces and remains adhered to the closure device at least until the wound dressing is applied. The coatings described also offer minimal resistance to closure device stretch (up to 50%) and themselves do not loose protective effects while the dressing is worn against the closure device.

Low Tack Adhesive Protective Strips.

According to further aspects of the present disclosure, one or more removable protective strips 201 of material (also referred to as "dressing shields") may be applied over the closure device 100 to protect the closure device from the adhesive of any wound dressing, as illustrated in FIGS. 2-5 for example. The protective strip(s) 201 may act as a sacrificial layer. The protective strip(s) 201 are preferably constructed from a material that does not stick to the underlying closure device 100. Each strip 201 may preferably be coated on the side facing the closure device 100 with the material that prevents adhesion to the closure device 100. The strip 201 may preferably be constructed from an elastic material 201a, for example, polyurethane, and may be coated with an adhesive 201b formulated and/or constructed to have lower tack to the closure device 100 than the closure device 100 has to skin, thus ensuring removal of the strips 201 does not disrupt adhesion of the closure device 100 to the skin. The strip 201 may be comprised of a single material layer with no adhesive, two layers where one layer is an adhesive or non-stick coating, or more than one material layer with the multiple layers laminated using heat or by incorporating a layer of adhesive between the layer(s), wherein the laminate adhesive may or may not be the same as the adhesive facing the closure device 100. In some embodiments, the strip 201 is a composite of elastic fibers, elastic film, and elastic adhesive. The strip 201 may comprise perforations, notches, cutout spaces (e.g., holes), and the like sufficiently sized to maximize elasticity and breathability of the strip 201 while minimizing the degree of adhesion from the dressing. The strip material may also comprise of a blown polyurethane film that is more elastic and porous for a given thickness than non-blown films, or other breathable non-woven material known in the art, typically fabricated from polyester, polyethylene, and polypropylene. The non-woven material may be constructed to be air permeable but not liquid permeable (without apertures) or may incorporate apertures for very high breathability and moisture transfer. The material could also be constructed from a woven fabric, preferably containing elastic fibers and/or antimicrobial coatings known in the art. Providing a very thin material (approximately 0.0005"-0.001") can aid in breathability and conformability, while thicker films or fabrics (up to approximately 0.025") may aid in user handling. The optimal design thickness may be in-between depending on desired elasticity and materials and construction chosen.

The strips 201 may be designed to ensure protection of the closure device but not interfere with the contact of the dressing with the wound or incision. As shown in FIG. 2, the outside of the strip 201 should not extend further than necessary beyond the outer perimeter 100c of the closure device 100 in order to maximize dressing contact with the skin. For a closure device 100 having a panel width of 17.5 mm, a 25 mm wide strip may be preferable to ensure optimal overlap of the strip and allow tolerance for hand alignment by the user. The strip length may be provided long enough to overlap the full length of the closure device 100 by approximately 5 mm on each end. The strip 201 may preferably be made from a material (e.g., thin polymer films) that can be trimmed to the desired length with surgical scissors.

Figure 3A:
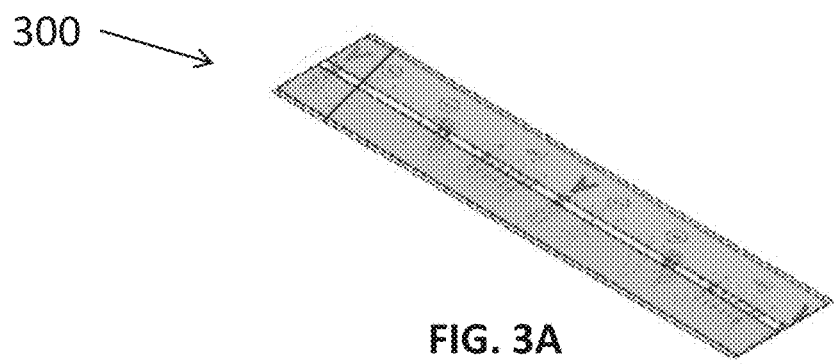
FIG. 3A shows a perspective view of a closure device and sacrificial cover strip assembly, according to many embodiments.
Figure 3B:
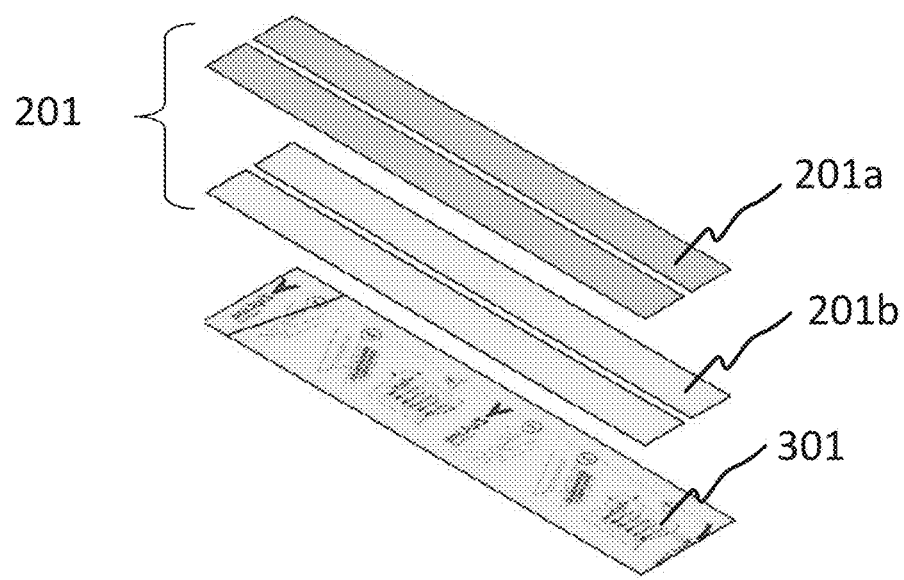
FIG. 3B shows an exploded view of the closure device and sacrificial cover assembly of FIG. 3A.

In some embodiments, as shown in FIGS. 3A and 3B, the strip 201 may comprises a 0.001" thick elastomeric film such as polyurethane film 201a coated with a 0.011" thick silicone adhesive as a gel or pressure sensitive adhesive 201b. The adhesive layer 201b may be protected with a release liner 301 until use. The silicone adhesive may preferably be constructed to be low tack such that it does not disrupt the closure device adhesive during removal. This may be achieved with the chemical formulation and/or by crosslinking the adhesive using irradiation such as electron beam or gamma. The silicone could also be formulated to be fully cured and/or cross-linked to have no adhesive properties.

In some embodiments, similar to the sacrificial cover strip assembly shown in FIGS. 3A and 3B, the strip 201 may comprise a 0.002" thick polyurethane film 201a with a low-tack 0.002" thick acrylic or urethane pressure sensitive adhesive (PSA) 201b applied to one side. The strip 201 may be supplied to the user with a release liner 301 to protect the adhesive until ready for application. The low-tack adhesive is formulated to be releasable from the surface of the closure device 100 (and patient's skin) before the closure device releases from the skin.

In some embodiments, illustrated in FIGS. 4A-5, a 25 mm wide strip 201 may comprise of a first 0.001" thick polyurethane film 201a and a second 0.001" thick polyurethane film 201c of the same size laminated to the first with a 0.002" acrylic PSA layer 201b therebetween. The second film 201c may be constructed to have notches 202 along the outer perimeter removed such that the PSA 201b may be exposed on one surface in the notch locations. As illustrated in FIGS. 4A-4C, the notches 202 may be approximately 2 mm×3 mm in size and spaced approximately 10 mm apart. By both controlling the notch size and recessing the adhesive below the surface of the second layer 201c, the strip 201 may provide the desired low tack sufficient to hold it in place against the closure device 100 and the desired release force of the strip 201 from the closure device 100 and skin. This may also allow the use of relatively strong PSA (e.g., the same formulation as used on the closure device 100) that will still release from the closure device 100. Other combinations of film thickness, notch size, cutout space, and adhesive strength may be achieved to a similar result. In other embodiments, the notches 202 or cutout spaces may be other shapes such as circles for holes, or may be closely spaced gaps between film strips 201.

Figure 6A:
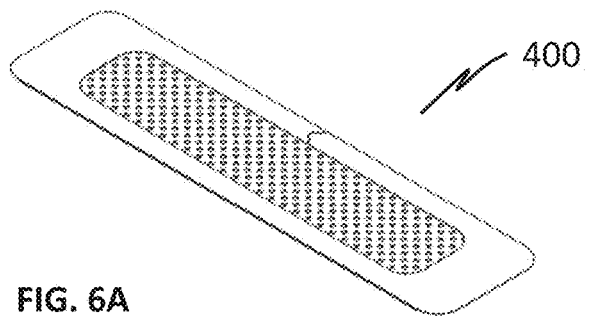
FIG. 6A shows a perspective view of a sacrificial cover strip assembly, according to many embodiments.
Figure 6B:
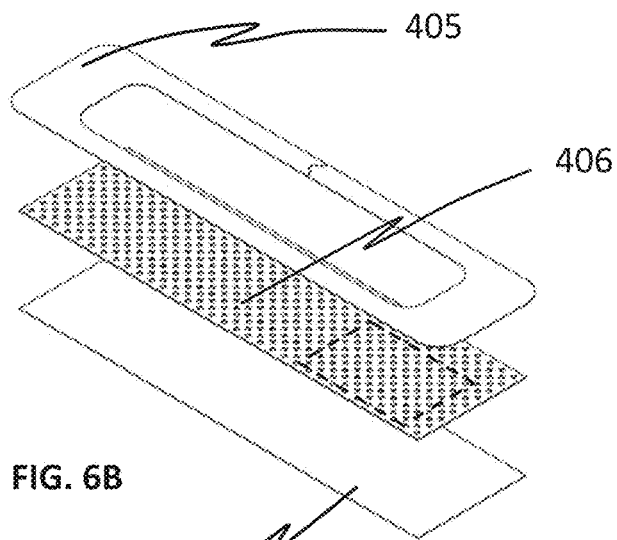
FIG. 6B shows an exploded view of the sacrificial cover strip assembly of FIG. 6A.
Figure 6C:
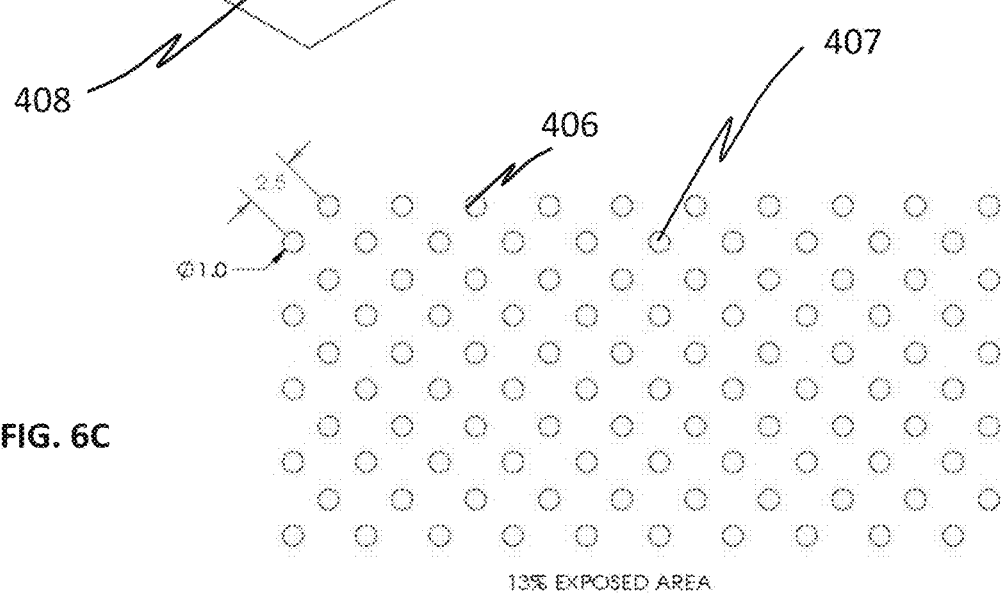
FIG. 6C shows apertures of the adhesive layer of the sacrificial cover strip assembly of FIG. 6A.

In some embodiments, shown in FIGS. 6A-6C, a single strip assembly 400 may be configured to cover the entire closure device 100 instead of comprising of the separate strips discussed previously. The single strip 400 may be provided with apertures 407 such that wound exudate may pass through the strip where it covers the incision. As illustrated in the exploded view of FIG. 6B, the strip assembly 400 may comprise an outer support film 405 lightly adhered to the outer surface of the strip material 406 to aid in placement of the strip. The support film 405 may then be removed by the user after placement. The support film 405 may be constructed from paper, polyethylene, or other suitable material. The support film 405 may preferably extend beyond the border of the strip 406 to aid in handling, but may also be die-cut to the same perimeter as the strip material 406. Similar to previous embodiments, the strip 400 may be provided with an adhesive layer, preferably a low-tack silicone adhesive as a gel or PSA protected by a release liner 408 until use. As illustrated in FIG. 6C, the apertures may preferably be approximately 1.0 mm in diameter and spaced approximately 2.5 mm apart for ~13% aperture exposure. The size and spacing of the apertures 407 may be varied to optimize exudate passage against protection of the closure device 100 surface. The aperture size and space may also be varied to optimize the low-tack silicone adhesive adhesion to be releaseable from the surface of the closure device 100 (and patient's skin) before the closure device 100 releases from the skin.

Figure 7A:
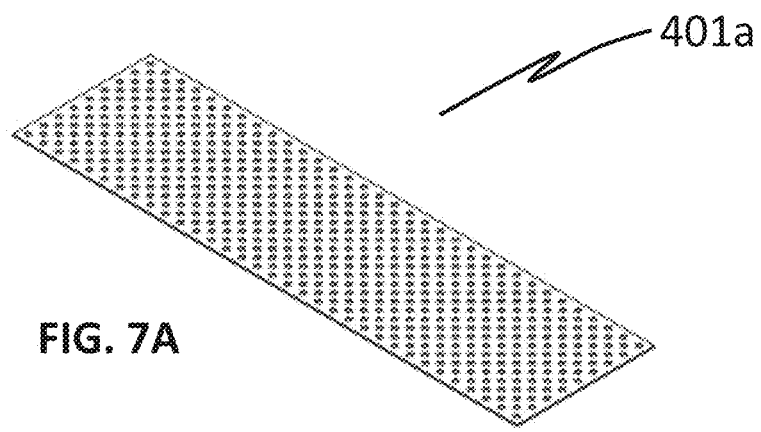
FIG. 7A shows a perspective view of a sacrificial cover strip assembly, according to many embodiments.
Figure 7B:
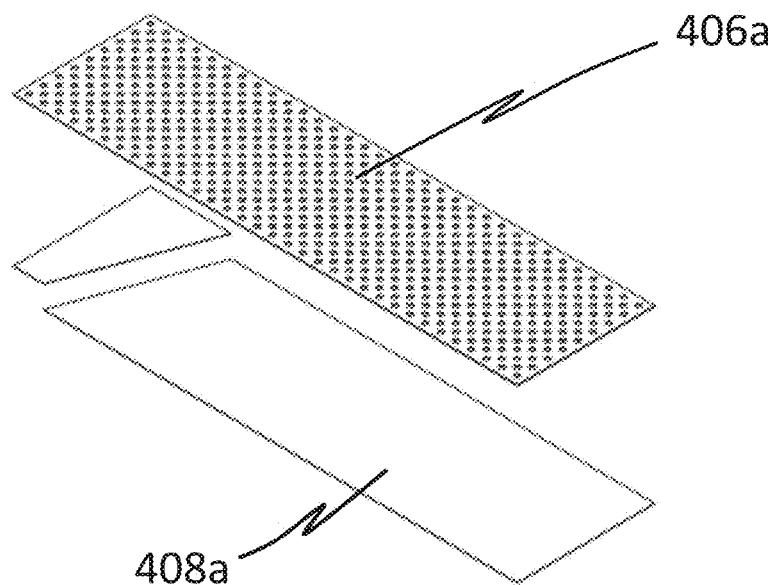
FIG. 7B shows an exploded view of the sacrificial cover strip assembly of FIG. 7A.

FIGS. 7A and 7B show a single strip assembly 401a similar to the single strip assembly 401 described above with respect to FIGS. 6A-6C. The single strip assembly 401a does not use a support frame 405. The release liner 408 in any of the above embodiments may incorporate a split or crack to aid in removal of the strip 406 from the release liner 408.

In embodiments similar to the above, the adhesive is applied to a single film (or film composite) in an interrupted pattern and/or discrete areas to minimize the total adhesive surface area to achieve low tack and optimal breathability.

For the above closure device protection embodiments, the method of application may be similar.

In a first step, the closure device may be applied to the patient, the closure device may be closed and have their straps cleaned, and the wound area may be cleaned.

In a second step, protective strip(s) 201 may be removed from the release liner 301 and applied over the outside of each base panel of the closure device 100 (e.g., base panels 102 and 104). The outer edges of the closure device 100 may be overlapped by the protective strip. The protective strip(s) may be lifted and repositioned as necessary.

In a third step, the wound dressing may be applied to the outside of the closure device 100 having the protective strips 201 in place.

In a fourth step, the wound dressing may be removed. The wound dressing may be removed prior to the removal of the closure device 100. The protective strips 201 may be removed along with the dressing, leaving the closure device 100 intact and adhered to the skin.

In a fifth step, if another dressing is required, new protective strips 201 may be placed over the closure device 100 and repeat the third step above may be repeated.

Figure 8A:
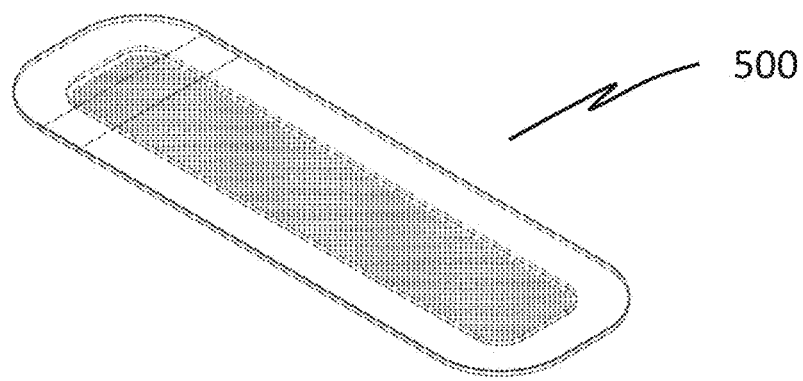
FIG. 8A shows a perspective view of a sacrificial cover strip assembly, according to many embodiments.
Figure 8B:
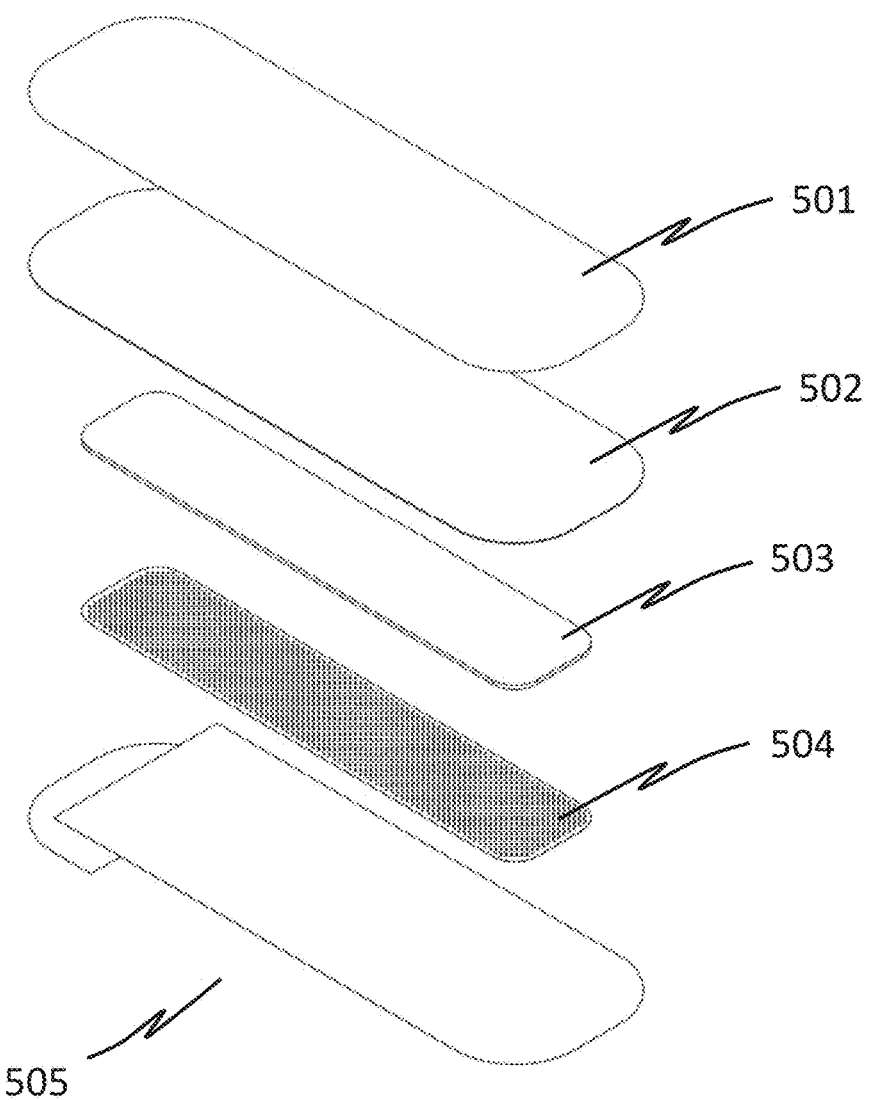
FIG. 8B shows an exploded view of the sacrificial cover strip assembly of FIG. 8A.

A protective layer similar to those described above with reference to FIGS. 6A-6C and FIGS. 7A-7B may be incorporated directly into the wound dressing to prevent the wound dressing from adhering to the closure device 100. FIGS. 8A-8B illustrate an exemplary island dressing 500 which may comprise a protective layer 504. The protective layer 504 may be similar in material and design as those described above with reference to FIGS. 6A-6C and FIGS. 7A-7B, except that the protective layer 504 may be adapted to be adhered to the exudate absorption layer 503 using PSAs, heat welding processes, or stitching techniques. Apertures in the protective layer 504 may allow passage of exudate into the absorption layer or exudate pad 503. The island dressing 500 may also include a skin adhesive layer 502 and protective film 501 to which the exudate pad 503 is adhered. Release liners 505 may protect the skin adhesive 502 and protective layer 504 until use. The protective layer 504 may also be of a construction similar to the sacrificial cover strip assembly 300 described above with reference to FIGS. 3A-3B, where two strips (each of which may or may not contain apertures) are adhered to the layer 503, with gap between the strips intended to align closely with the incision and encourage unimpeded passage of exudate.

Figure 9A:
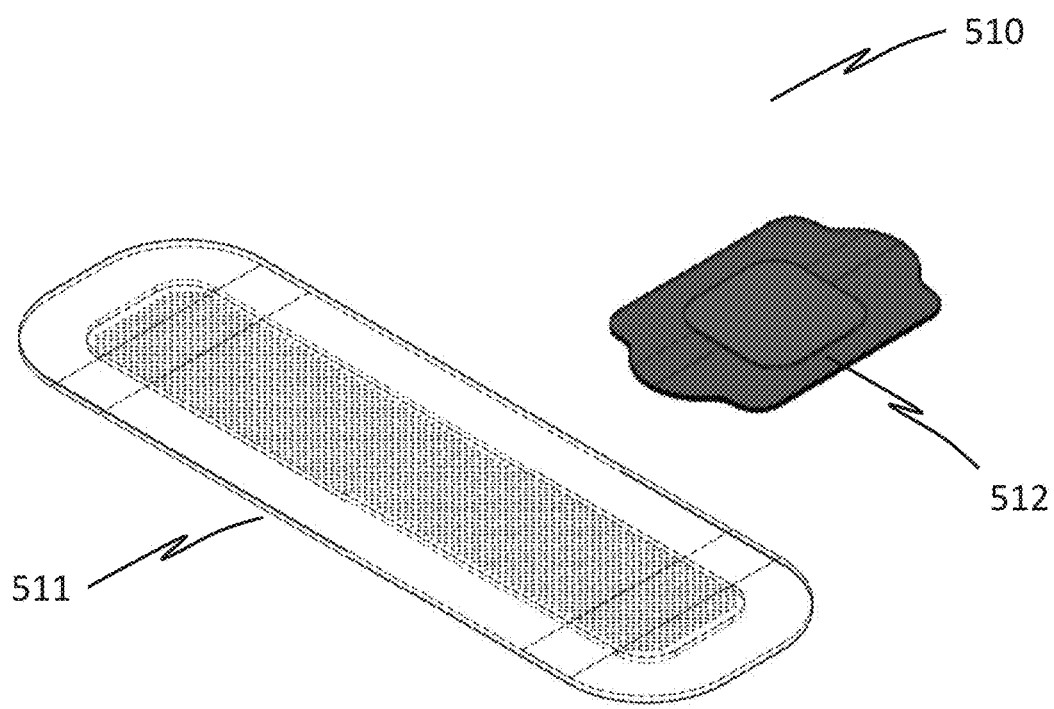
FIG. 9A shows a perspective view of a modular wound dressing assembly with a protective layer, according to many embodiments.
Figure 9B:
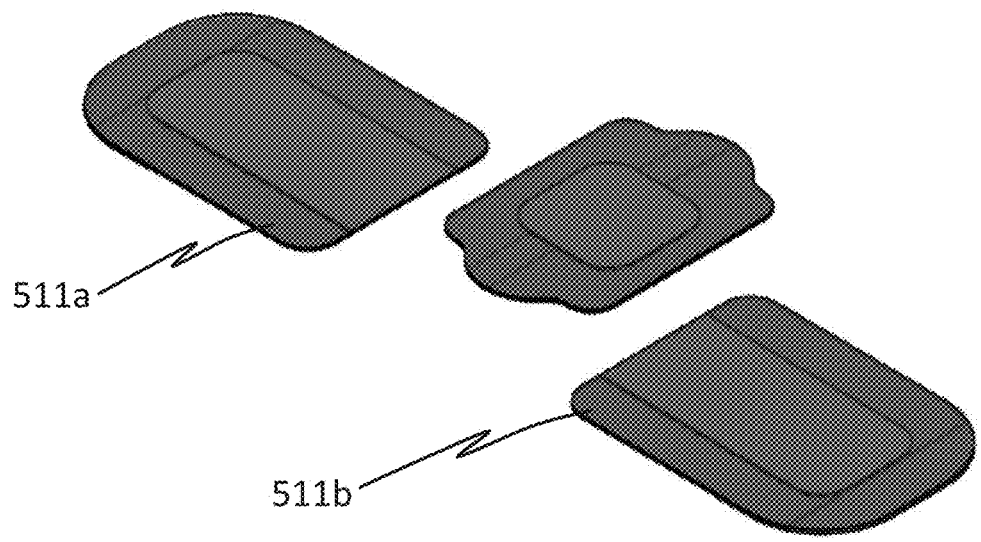
FIG. 9B shows an exploded view of the modular wound dressing assembly of FIG. 9A.
Figure 9C:
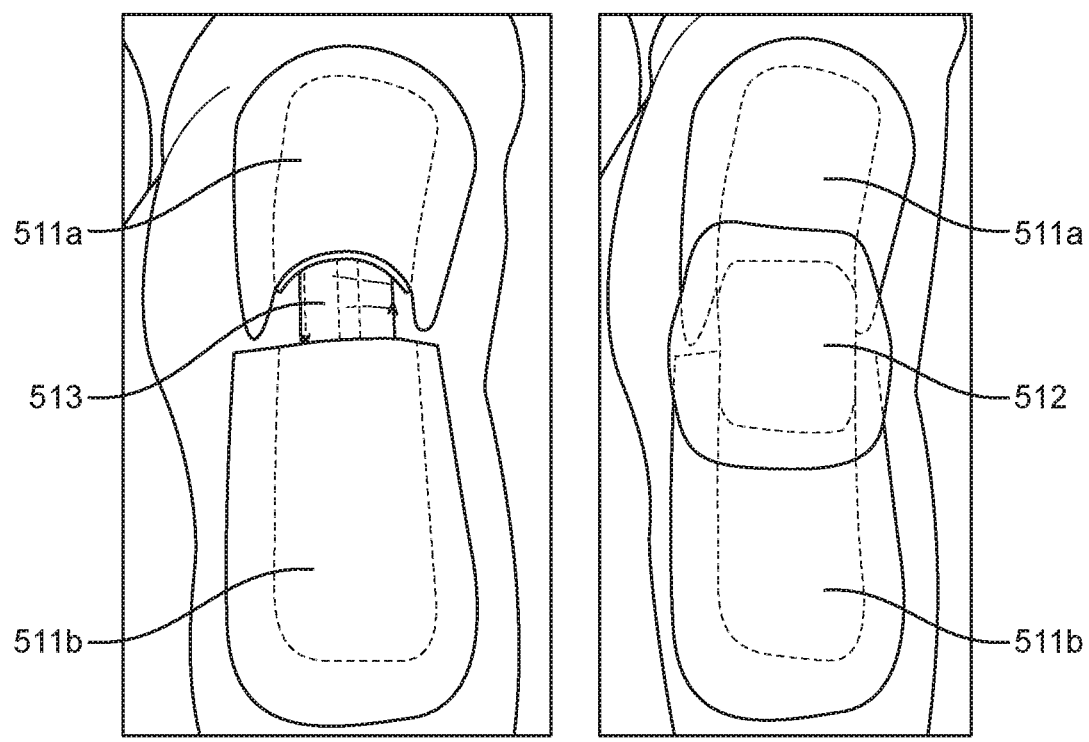
FIG. 9C shows placements of the modular wound dressing assembly of FIG. 9A on a knee.

As illustrated in FIGS. 9A-9B, a dressing 510 may be provided in two parts, first part 511 and second port 512. The first part 511 may be provided in a construction similar to that of dressing 500 in FIGS. 8A-8B, except that a short release liner portion of 505 is provided on each end, with a longer release liner between. This first part 511 may be cut transversely by the user into two parts 511a and 511b at a desired location between the short release liners. Alternatively, the first part may be provided to the user pre-cut in two parts 511a and 511b as illustrated in FIG. 9B. The user may then trim one or both of the two cut first parts to a shorter length as desired, such that the two cut lengths are shorter than the total closure device length by an amount less than the length of the provided second device part 512. As illustrated in FIG. 9C, a selected first part 511a may be applied to the skin overlapping one end of the closure device, after first removing the small release liner. The remainder of the longer release liner can then be removed and the remainder of the cut first part 511a is adhered over the incision and Zip device. The remaining cut first part 511b is then applied in a similar manner beginning at the opposite end of the incision and closure device. The second part 512 may then be applied over the gap 513 between the two applied first parts such that the second part overlaps the ends of the two cut first parts. The advantage of this configuration and application technique may be that the user may easily center the cut first parts of the dressing over the closure device. Another advantage can relate to placement over a joint. The two cut first parts may be applied over the ends of the incision on either side of the joint in a manner that relatively few folds in the dressing are required. The uncovered section over the joint may then be covered with the shorter second part where the folds are more easily managed. Managing the folds can be important to minimize folds and to tightly crease them to minimize ingress or egress of fluids or other contamination in spaces formed by the folds.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A method of closing an incision or wound, the method comprising:
    adhering first and second base panels of a closure device to tissue adjacent first and second lateral sides, respectively, of the incision or wound, wherein the first and second base panels are coupled to one another by a plurality of lateral ties coupled to each of the first and second base panels;
    positioning one or more sacrificial cover strips over the first and second base panels that are adhered to the tissue, wherein the one or more sacrificial cover strips adhere to the first and second base panels; and
    positioning a wound dressing over the one or more sacrificial cover strips that are adhered to the first and second base panels, wherein the wound dressing adheres to the one or more sacrificial cover strips, and
    wherein the one or more sacrificial cover strips allow the wound dressing to be removed while leaving the closure device adhered to the tissue,
    wherein positioning the wound dressing over the one or more sacrificial cover strips comprises placing a first dressing part over a first longitudinal portion of the closure device and placing a second dressing part over a second longitudinal portion of the closure device, the second longitudinal portion being opposite the first longitudinal portion,
    wherein the first and second dressing parts are longitudinally separate from one another to allow longitudinal separation therebetween when the closure device adhered to the tissue stretches longitudinally,
    wherein the first and second dressing parts each span between the first and second base panels to be positioned over the lateral ties and the incision or wound to absorb exudate therefrom, and
    wherein the one or more sacrificial strips comprise upper adhesive surfaces having a first adhesive tack and lower adhesive surfaces having a second adhesive tack less than the first adhesive tack.

2. The method of claim 1, wherein positioning the one or more sacrificial cover strips over the first and second base panels comprises extending perimeters of the one or more sacrificial cover strips over perimeters of the first and second base panels.

3. The method of claim 2, wherein the one or more sacrificial cover strips overlap full lengths of one or more of the first or second base panels.

4. The method of claim 1, wherein the one or more sacrificial cover strips comprise one or more perforations, notches, or cutout spaces.

5. The method of claim 1, wherein the one or more sacrificial cover strips comprise an elastic film layer.

6. The method of claim 1, wherein the one or more sacrificial cover strips comprise a pressure sensitive adhesive layer.

7. The method of claim 1, further comprising removing a release liner from the one or more sacrificial cover strips prior to the one or more cover strips being adhered to the first and second base panels.

8. The method of claim 1, wherein at least a portion of the first or second dressing part overlaps with the other.

9. The method of claim 1, wherein positioning the wound dressing over the one or more sacrificial cover strips comprises placing a third dressing part longitudinally between the first and second dressing parts.

10. The method of claim 1, wherein each of the base panels comprises a plurality of force distribution structures distributed along a length thereof.

11. The method of claim 10, wherein the plurality of lateral ties are coupled to the force distributions structures of the first and second base panels.

12. The method of claim 11, wherein each lateral tie couples laterally adjacent force distribution structures of the first and second panels to one another.

13. The method of claim 10, wherein the plurality of force distribution structures are coupled to upper surfaces of the first and second base panels.

* * * * *